(12) United States Patent
Anthapur

(10) Patent No.: US 12,148,527 B2
(45) Date of Patent: Nov. 19, 2024

(54) SENSOR-BASED MONITORING OF AT-RISK PERSON AT A DWELLING

(71) Applicant: Zemplee Inc., Campbell, CA (US)

(72) Inventor: Aparna Pujar Anthapur, Campbell, CA (US)

(73) Assignee: Zemplee Inc., Campbell, CA (US)

( * ) Notice: Subject to any disclaimer, the term of this patent is extended or adjusted under 35 U.S.C. 154(b) by 399 days.

(21) Appl. No.: 17/578,188

(22) Filed: Jan. 18, 2022

(65) Prior Publication Data

US 2022/0230746 A1    Jul. 21, 2022

Related U.S. Application Data

(60) Provisional application No. 63/199,672, filed on Jan. 15, 2021.

(51) Int. Cl.
*G16H 40/67* (2018.01)
*G08B 21/04* (2006.01)

(52) U.S. Cl.
CPC ......... *G16H 40/67* (2018.01); *G08B 21/0415* (2013.01); *G08B 21/0423* (2013.01)

(58) Field of Classification Search
CPC .................................................... G16H 40/67
See application file for complete search history.

(56) References Cited

U.S. PATENT DOCUMENTS

| | | | | |
|---|---|---|---|---|
| 8,604,932 B2* | 12/2013 | Breed | ..................... | G01S 17/88 |
| | | | | 340/576 |
| 10,037,673 B1* | 7/2018 | Gray | ..................... | G08B 21/22 |
| 11,581,099 B1* | 2/2023 | Rufo | ..................... | G16H 20/13 |
| 2006/0055543 A1* | 3/2006 | Ganesh | .............. | G08B 21/0423 |
| | | | | 340/526 |
| 2006/0058704 A1* | 3/2006 | Graichen | ........... | G08B 21/0469 |
| | | | | 600/595 |
| 2007/0194922 A1* | 8/2007 | Nathan | .................. | A62B 99/00 |
| | | | | 340/8.1 |
| 2011/0241877 A1* | 10/2011 | Wedig | ..................... | G08B 17/00 |
| | | | | 340/540 |
| 2012/0136667 A1* | 5/2012 | Emerick | ................. | G16H 20/40 |
| | | | | 704/E21.001 |
| 2016/0314255 A1* | 10/2016 | Cook | ..................... | G06F 16/906 |
| 2017/0105080 A1* | 4/2017 | Das | ........................ | G10L 25/51 |
| 2019/0122522 A1* | 4/2019 | Stefanski | ........... | G08B 21/0423 |
| 2019/0236923 A1* | 8/2019 | Devdas | .................. | A61B 5/1113 |
| 2020/0211358 A1* | 7/2020 | Burke | .................. | G08B 21/043 |

(Continued)

*Primary Examiner* — Travis R Hunnings
(74) *Attorney, Agent, or Firm* — Schwegman Lundberg & Woessner. P.A

(57) ABSTRACT

A method is provided to monitor a resident of a dwelling comprising: using a sensor located at the dwelling to sense for resident activity at a location at the dwelling; using a machine learning trained model, trained based at least in part upon resident activity at the location at the dwelling sensed by the sensor to learn an anticipated time of resident activity at the location of the dwelling, to identify the anticipated time of occurrence of resident activity at the location at the dwelling; determining whether the sensor information indicates an occurrence of the anticipated resident activity; and sending an alert indicating a failed anticipated activity event, on a condition that the sensor data indicates none occurrence of the anticipated resident activity.

19 Claims, 30 Drawing Sheets

(56) References Cited

U.S. PATENT DOCUMENTS

| | | | |
|---|---|---|---|
| 2022/0188716 A1* | 6/2022 | Mathieu | G16H 50/30 |
| 2023/0317269 A1* | 10/2023 | Davis | G06N 5/022 |
| | | | 705/2 |

\* cited by examiner

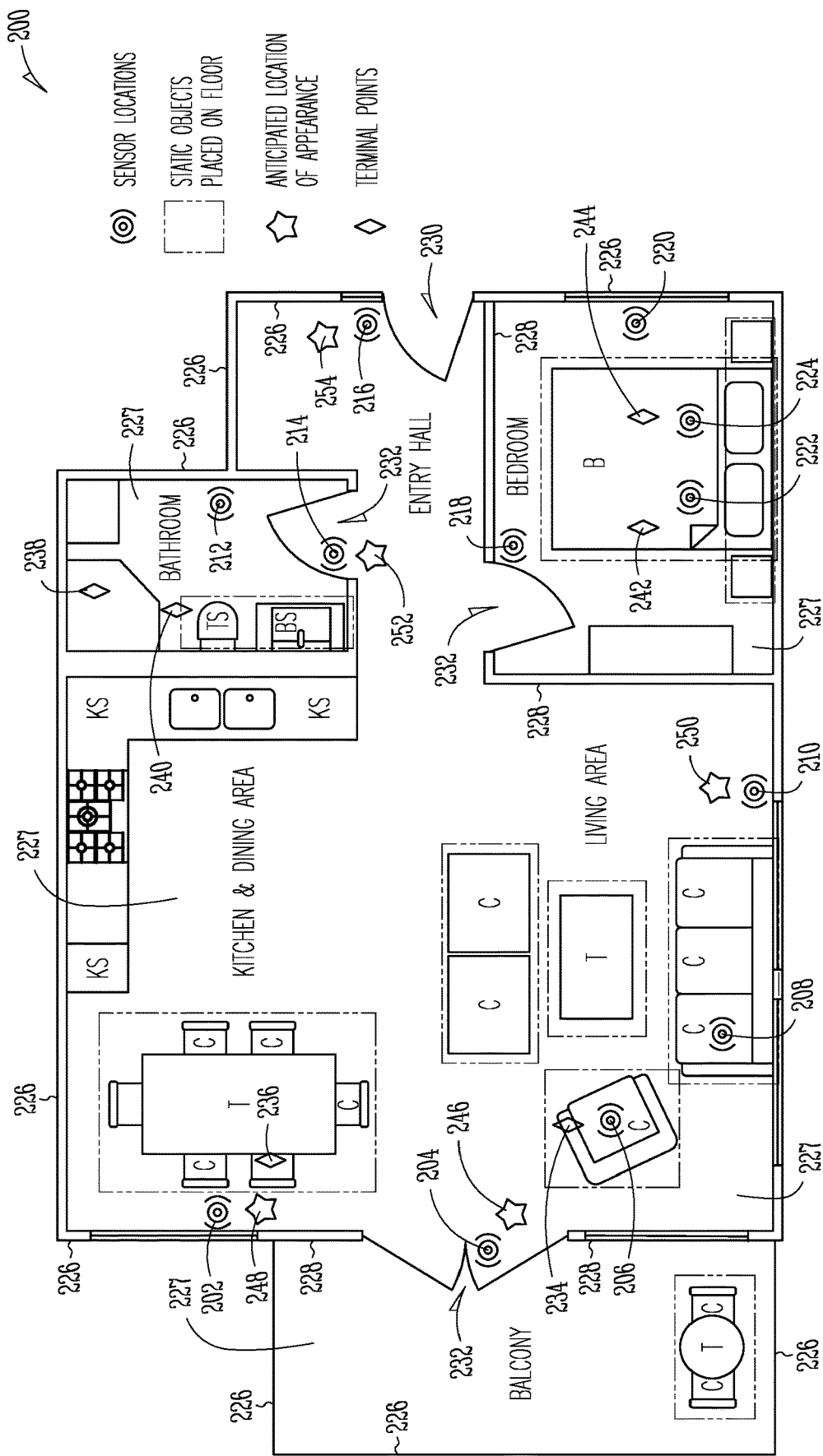

| TERMINAL POINT FROM | TIME OF DAY (TOD) | DAY OF WEEK (DOW) | TERMINAL POINT TO | RISK SCORE | LEGEND |
|---|---|---|---|---|---|
| C145-02345672 | 05300800 | SU-1 | C145-02345675 | 67.23% | LIVING ROOM CHAIR TO KITCHEN, EARLY MORNING |
| C145-02345672 | 17302000 | WE-4 | C145-02345676 | 73.44% | LIVING ROOM CHAIR TO BATHROOM, TWILIGHT |
| C145-02345672 | 11001300 | MO-2 | C145-02345677 | 40.23% | LIVING ROOM CHAIR TO BEDROOM |
| C145-64301964 | 05300800 | FR-6 | C145-02345676 | 87.03% | BEDROOM BED TO BATHROOM, EARLY MORNING |
| C145-64301964 | 14001600 | TH-5 | C145-02345675 | 36.33% | BEDROOM BEDMAT TO KITCHEN |
| C145-64301964 | 12000600 | FR-6 | C145-02345675 | 87.03% | BEDROOM BED TO LIVING ROOM, LATE NIGHT |
| C145-64301964 | 05300800 | SA-7 | C145-02345675 | 48.56% | BEDROOM BED TO LIVING ROOM, EARLY MORNING |
| C145-64301964 | 12000600 | FR-6 | C145-01847262 | 98.56% | BEDROOM BED TO FRONT DOOR, LATE NIGHT |
| C145-02345676 | 12000600 | SU-1 | C145-64301964 | 94.99% | BATHROOM TO MASTER BEDROOM, LATE NIGHTS |
| C145-02345676 | 12000600 | MO-2 | C145-64301964 | 94.99% | BATHROOM TO MASTER BEDROOM, LATE NIGHTS |
| C145-02345676 | 12000600 | TU-3 | C145-64301964 | 94.99% | BATHROOM TO MASTER BEDROOM, LATE NIGHTS |
| C145-02345676 | 12000600 | WE-4 | C145-64301964 | 94.99% | BATHROOM TO MASTER BEDROOM, LATE NIGHTS |
| C145-02345676 | 12000600 | TH-5 | C145-64301964 | 94.99% | BATHROOM TO MASTER BEDROOM, LATE NIGHTS |
| C145-02345676 | 12000600 | FR-6 | C145-64301964 | 94.99% | BATHROOM TO MASTER BEDROOM, LATE NIGHTS |
| C145-02345676 | 12000600 | SA-7 | C145-64301964 | 94.99% | BATHROOM TO MASTER BEDROOM, LATE NIGHTS |

Fig. 4

DEACTIVATE MONITORING

ARE YOU SURE YOU WISH TO TURN OFF MONITORING?

SELECT REASON
[HOSPITALIZATION ▼]

ENTER DETAILS

RESTART IN
[30 MINUTES ▼]

[YES] [NO]

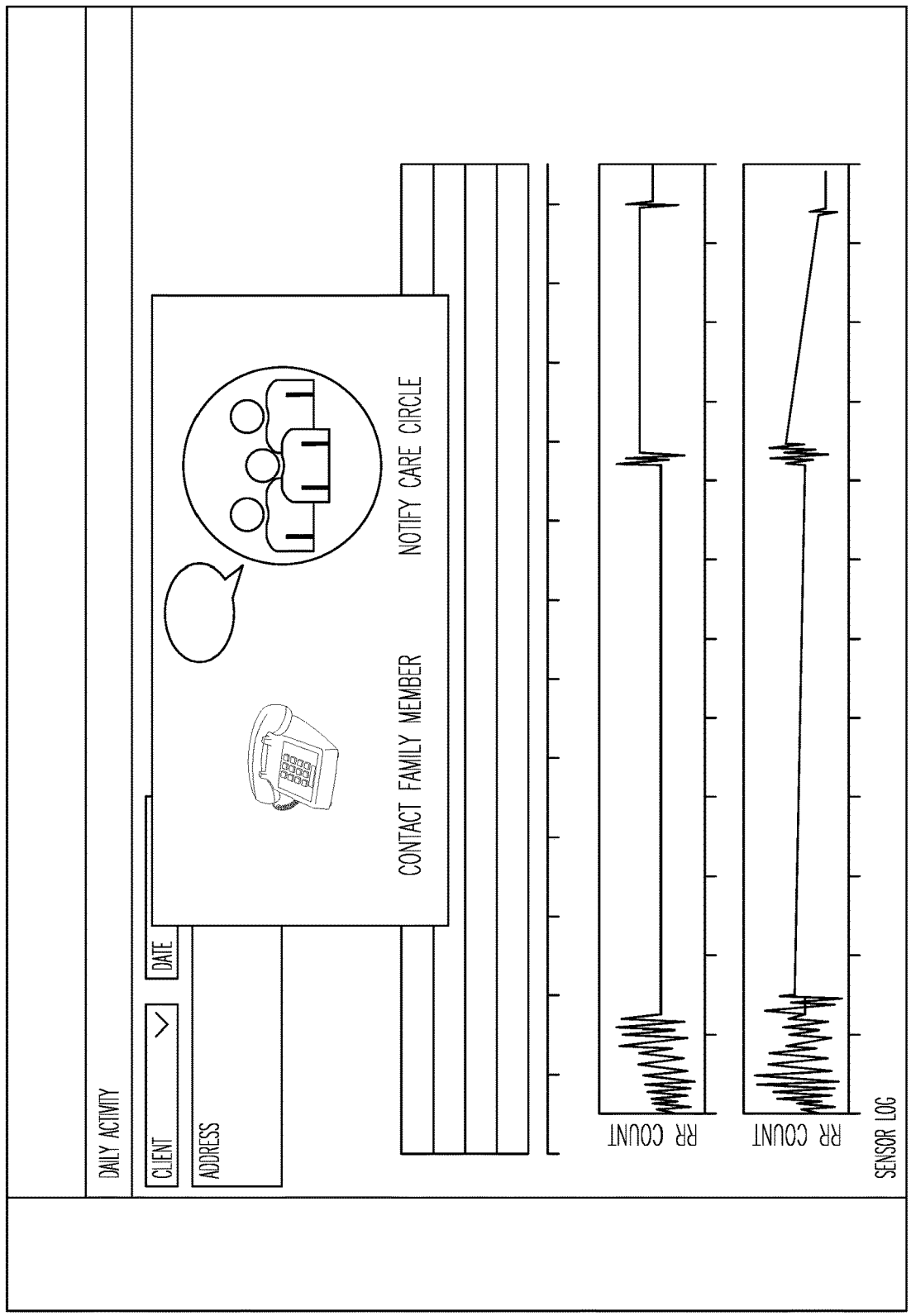

SENSOR-BASED MONITORING OF AT-RISK PERSON AT A DWELLING

CROSS-REFERENCE TO RELATED APPLICATION

This application claims priority to U.S. provisional application Ser. No. 63/199,672, filed Jan. 15, 2021, entitled, Motion Sensing Ambulation Pattern Detection and Mapping for Seniors Identifying Falls or Other Ambulatory Disablement, which is incorporated herein in its entirety by this reference.

BACKGROUND

Most elderly wish to live, age in place and end-well. By the Year 2050, more than one fifth of the population will be over the age of 65 and 80% of these seniors will be living alone out of necessity or choice. While living alone, they need to be able to perform activities of daily living, household chores and manage their health, safety and wellbeing. As their physical ability deteriorates from age related atrophy, they are susceptible to fall risks and other accidents. Families who take on the responsibility of elderly care are under constant stress and duress from the possibility that their elderly loved one is in constant state of endangerment to themselves. They may be involved in a fall incident, resulting in a life-threatening injury, causing them to be stuck in a location for hours because of their inability to move.

Numerous personal tracking and monitoring technologies are being developed to address unique challenges created by the aging population. Emergencies related to fall or ambulatory disruptions can happen suddenly and without a warning. Current solutions include technology products that need to be physically worn—like a wristwatch or be carried on their person like a key fob placed in a shirt pocket or handbag, or a pendant worn around the neck. However, such products can become useless. If a senior person's arm is broken or the senior suffers from a head injury that results in unconsciousness because of the accident, they will not have the ability to press or activate these devices and summon help. It is also possible, the device may not be on their person or in vicinity at the time of the accident, in order for them to activate it and get help.

Adapting to new technology products requires a significant lifestyle change and continued education. Often, it is accompanied by the need to perform important tasks—like charging the device periodically or replacing the batteries that power these devices.

It is estimated that by 2050, the total number of people with dementia is expected to reach 152M. Dementia prevalence increases with age, from 5.0% of those aged 71-79 years to 37.4% of those aged 90 and older. Vision loss and hearing loss further adds to the challenge and diminishes an elderly's ability to respond to visual or audio prompts or signals.

Furthermore, there is a psychological resistance or stigma associated with adorning some of these devices. Elders rarely want to broadcast to the world of the state of their decline. They expect to be treated with dignity. The elderly also may choose not to report fall incidents or ambulatory degeneration for hesitation of creating unnecessary concern for their family members, or from fear of being forced into a communal care setting which threatens their independence.

Most fall incidents happen during a transition from a static state, for example when the elderly attempt to get up from their bed, chair, or toilet seat to walk to another location. The current solutions fall short, especially during nocturnal hours, when the risk for accidents is the highest and devices are not on person or in proximity.

To ensure all round coverage in a private, non-invasive, non-intrusive way, passive monitoring of the elderly in their dwelling unit is needed.

SUMMARY

In one aspect, a system is provided to monitor a resident of a dwelling. A plurality of sensors located at the dwelling sense resident activity at different locations at the dwelling and save in non-transitory memory, sensor information providing indications of occurrences resident activity. One or more computing machines are configured with instructions to perform operations. An operation identifies a location at the dwelling, of resident activity, based at least in part upon sensor information produced using a sensor located at the dwelling to sense resident activity at the identified location. An operation use a machine learning trained model, trained based at least in part upon resident traversal activity between sensors at different locations of the dwelling to learn a plurality of anticipated traversal paths (ATPs) located at the dwelling each ATP having a first terminal point and a second terminal point, to identify one or more ATPs based at least in part upon the identified location, the one or more identified ATPs each having a first terminal points associated with the identified location and having a second terminal point associated with a different location at the dwelling. An operation determines whether the sensor information indicates an occurrence of resident activity at a location at the dwelling corresponding to a second terminal point of at least one of the one or more identified ATPs. An operation cause sending of an alert indicating a failed ATP traversal event, on a condition that the sensor data indicates for each of the one or more identified ATPs, no occurrence of resident activity at a location of the dwelling corresponding to the second terminal point of the identified ATP.

In another aspect a system to monitor a resident of a dwelling. A sensor located at the dwelling senses resident activity at a location at the dwelling saves at non-transitory memory, sensor information providing an indication of resident activity and time of resident activity at the location at the dwelling. One or more computing machines are configured with instructions to perform operations. An operation uses a machine learning trained model, trained based at least in part upon resident activity at the location at the dwelling sensed by the sensor to learn an anticipated time of resident activity at the location of the dwelling, to identify the anticipated time of occurrence of resident activity at the location at the dwelling. An operation determines whether the sensor information indicates an occurrence of the anticipated resident activity within a predetermined time interval after the anticipated time of occurrence of the resident activity at the location at the dwelling. An operation causes sending of sending of an alert indicating a failed anticipated activity event, on a condition that the sensor data indicates no occurrence of the anticipated resident activity within the predetermined time interval after the anticipated time.

In another aspect, a system is provided to monitor a resident of a dwelling. A plurality of sensors located at the dwelling sense resident activity at different locations at the dwelling save sensor information providing an indication of occurrences and times of resident activity at the different locations at the dwelling. One or more computing machines are configured with instructions to perform operations. An operation uses a machine learning trained model, trained based at least in part upon resident traversal activity between sensors at different locations of the dwelling to learn an anticipated traversal path ATP located at the dwelling the ATP having a first terminal point and a second terminal point and to learn a path traversal frequency (PTF) for the learned ATP, to identify the PTF for the ATP. An operation determines whether the sensor information indicates resident traversal of the ATP with a frequency that is within a predetermined range of the PTF. An operation causes sending of an alert indicating a failed PTF event, on a condition that the sensor data indicates resident traversal of the ATP is not within the predetermined range of the PTF.

BRIEF DESCRIPTION OF THE DRAWINGS

Some embodiments are illustrated by way of example and not limitation in the figures of the accompanying drawings. In the drawings, which are not necessarily drawn to scale, like numerals may describe similar components in different views. Like numerals having different letter suffixes may represent different instances of similar components.

FIG. 2 is an illustrative drawing showing a top elevation view of a second example dwelling in which multiple sensors are located to sense health status and activity of a resident at the dwelling.

FIG. 4 is an illustrative chart representing example risk scoring of ATPs.

FIG. 10 is an example user interface display used for initiation and de-initiation of the hibernation process.

FIG. 15B is an illustrative drawing representing an example alert message displayed in an Alerts Dashboard of an example web application.

FIG. 16A and FIG. 16B are illustrative drawings representing an example Family and Caregiver Daily Activity Dashboard Page (FIG. 16A) and an example Patient Activity Dashboard Page respectively in the web client or mobile application (FIG. 16B).

DETAILED DESCRIPTION

The example embodiments described herein seek to address the need and desire of at-risk persons such as the elderly to stay independently in their choice of dwelling, while enabling members of their care circle to receive communication through various modalities such a text message, push notification or a phone call, when an unexpected accident that can be life threatening or can cause a temporary or permanent disablement to the senior occurs. The communication needs to occur in in a timely manner so appropriate action can be taken to remediate the situation and ensure that the at-risk person is out of danger.

Figure 1A:
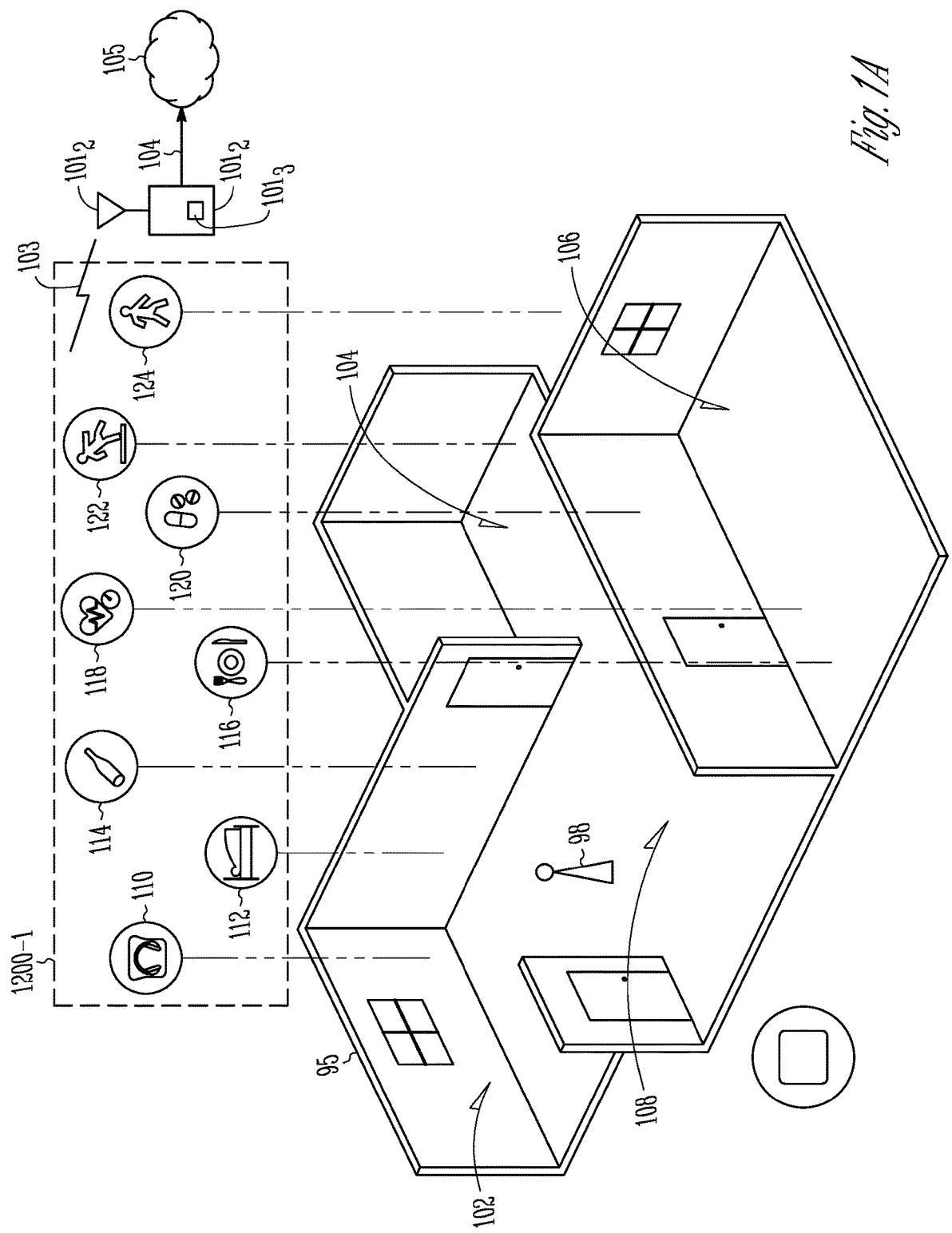
FIG. 1A is an illustrative drawing showing a perspective partially cutaway view of a first example dwelling in that includes a sensor system to sense health status and activity of a resident within the dwelling.
Figure 1B:
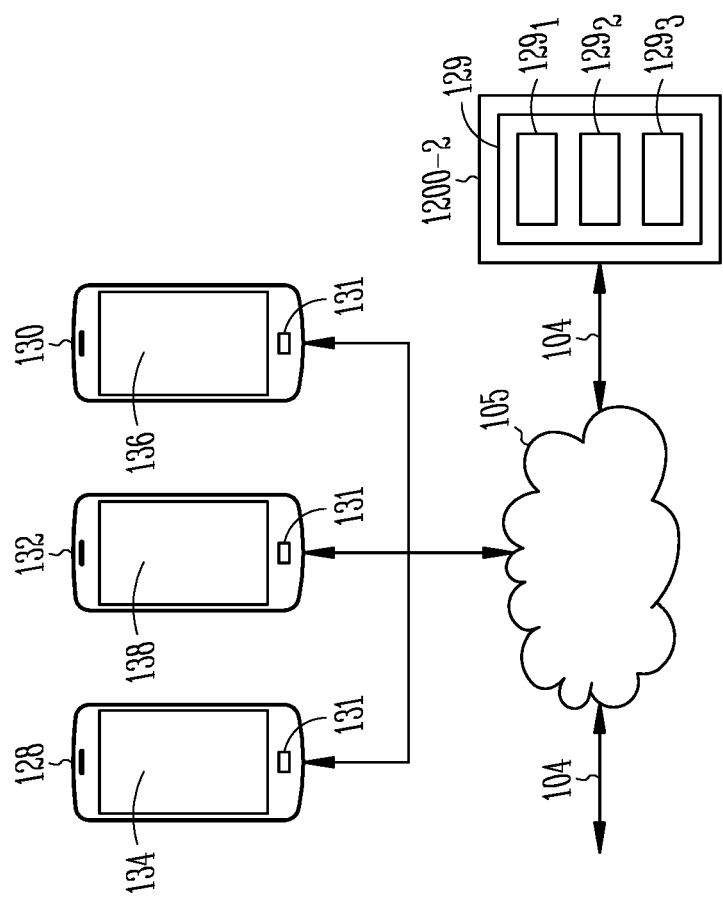
FIG. 1B is an illustrative drawing representing an information processing system and user communication devices coupled to communicate to with the sensor system of FIG. 1A.

FIG. 1A is an illustrative drawing showing a perspective partially cutaway view of a first example dwelling 95 in that includes an example sensor system 1200-1 that includes multiple sensors 110-124 that are located to sense health status and activity of an at-risk person 98, referred to herein as a "resident", within the dwelling 95. FIG. 1B is an illustrative drawing representing an example sensor data processing and communication system 1200-2 and mobile user communication devices 128, 132, 134 coupled to communicate to via the network 105 with the sensor system 1200-1 of FIG. 1A, The example sensor system 1200-1 and the example sensor data processing and communication system 1200-2 are portions of an example monitoring system 1200 described more fully below with reference to FIGS. 13A-13B. A network communication device $101_1$ including an antenna $101_2$ that is coupled to wirelessly communicate information 103 to and from the sensors 110-124 and is coupled to communicate information 104 over a network 105, such as the Internet, to and from a sensor data processing and communication system 1200-2. The network communication device also includes non-transitory memory $101_3$ to temporarily store sensor measurement data and time stamp data. An example network communication device $101_1$ can include a wireless router. The sensor data processing and communication system 1200-2 is configured to communicate information over the network 105 to and from one or more at a time of multiple user devices 126, 128, 130 that include respective display screens 132, 134, 136. An example user device can include a smart phone, a portable media device, a desktop computer, a vehicle computer, a tablet computer, a navigational device, or a wearable device (e.g., a smart watch, smart glasses, or smart clothing) belonging to a user.

Referring to FIG. 1A, the example dwelling 95 includes four areas: a bedroom 102, a bathroom 104, a kitchen/dining room 106, and a center hallway 108, which is located between the other areas. An example first weight measuring sensor 110 is located by the bed to automatically measure a person's weight. An example second is vital signs sensor 112 is located on a bed to sense occupancy and vitals such as sleep, heart rate and respiratory rate. An example third temperature measuring device, such as thermometer sensor 114 is located on a bedside table to automatically measure temperature. An example fourth open/close sensor 116, is located on a refrigerator or food storage cabinet to sense activity that determines intent to nourish or hydrate. An example fifth sensor, such as a blood pressure measuring device 118, is located in the vicinity of the living room to automatically measure blood pressure. An example sixth open/close sensor 120 is located on a medicine chest or a pill box to sense an action that determines intent to medicate. An example seventh motion sensor 122 is located in bathroom to automatically sense movement or a lack of movement or activity. An example eighth motion sensor 124 is located in a living room to automatically sense movement or a lack of movement or activity.

Referring to FIG. 1B, an example sensor data processing and communication system 1200-2 includes one or more computing machines that use machine learning techniques to evaluate information received from one or more of the example sensors 110-124 to determine the safety status of a resident 98 within the dwelling 95. The sensors 110-124 automatically produce sensor information 103 indicative of activity of a resident within the dwelling 95, which can be transmitted using the network device $101_1$, over the network 105 to sensor data processing and communication system 1200-2. More particularly, in an example monitoring system, individual sensors locally store measurement information in local non-transitory memories (not shown) for later transmission over the network 105 to the sensor data processing and communication system 1200-2 for evaluation. The sensor data processing and communication system 1200-2 uses the sensor information to evaluate the health and safety status of the resident 98. The sensor data processing and communication system 1200-2 sends information over the network 105 to one or more of the user devices 128, 130, or 132 based upon the sensor information. The sensor data processing and communication system 1200-2 can send different information to different user devices.

More particularly, the sensor data processing and communication system 1200-2 is configured to execute instructions stored in a non-transitory memory to run a computer monitoring and control application 129, which comprises a computer program that includes different monitoring and computer program control modules $129_1, 129_2, 129_3$ that are accessed and operated based upon type of user login. Different monitoring and control modules provide access to different information and support different functions. The example mobile devices each includes an instance of a mobile client application 131 to communicate with different monitoring and control modules $129_1, 129_2, 129_3$ based upon login type. In an example monitoring application, an example first monitoring and control module $129_1$ is a family member login type for access and operation by a person logging in as family member of the resident. An example second monitoring and control module $129_2$ is a professional care provider login type for access and operation by a person logging in as a professional care provider of the resident. An example third monitoring and control login module $129_3$ is a payor (e.g., an insurer) for access and operation by a person logging in as a payor for services provided to the resident.

In response to a family member login type login to the application 129 at a first user device 128, computer instructions stored in a nontransitory memory and configure the device 128 to implement the first monitoring and control module $129_1$ cause the sensor data processing and communication system 1200-2 to immediately send to a client application instance 131 at the first device 128, alert notifications of certain critical events, such as a fall incident, that require a prompt response. The first monitoring and control module $129_1$ also causes the sensor data processing and communication system 1200-2 to periodically send to the client application instance 131 at device 128, a consolidated report of the health status and activity of a resident. The reports of certain critical events that need attention, such as a fall incident, are sent as alert notifications in real time. Consolidated reports of the health status and activity meant to help discover underlying conditions and remediate through interventions, may be sent at periodic intervals such as daily, for example.

In response to a professional care provider login type login type login to the application 129 at a second user device 130, computer instructions stored in a nontransitory memory and configure the device 128 to implement the second monitoring and control module $129_2$ cause the sensor data processing and communication system 1200-2 to immediately send to a client application instance 131 at the second device 130, alert notifications of certain critical events, such as a fall incident, to periodically send (e.g., daily) a summary of the different types of alerts, resolution made by monitoring agents on the alerts, a summary of health parameters collected from the devices, histograms of health parameters and recommendations based upon Artificial Intelligence (AI) algorithms on creating or modifying care plans on record.

Figure 15A:
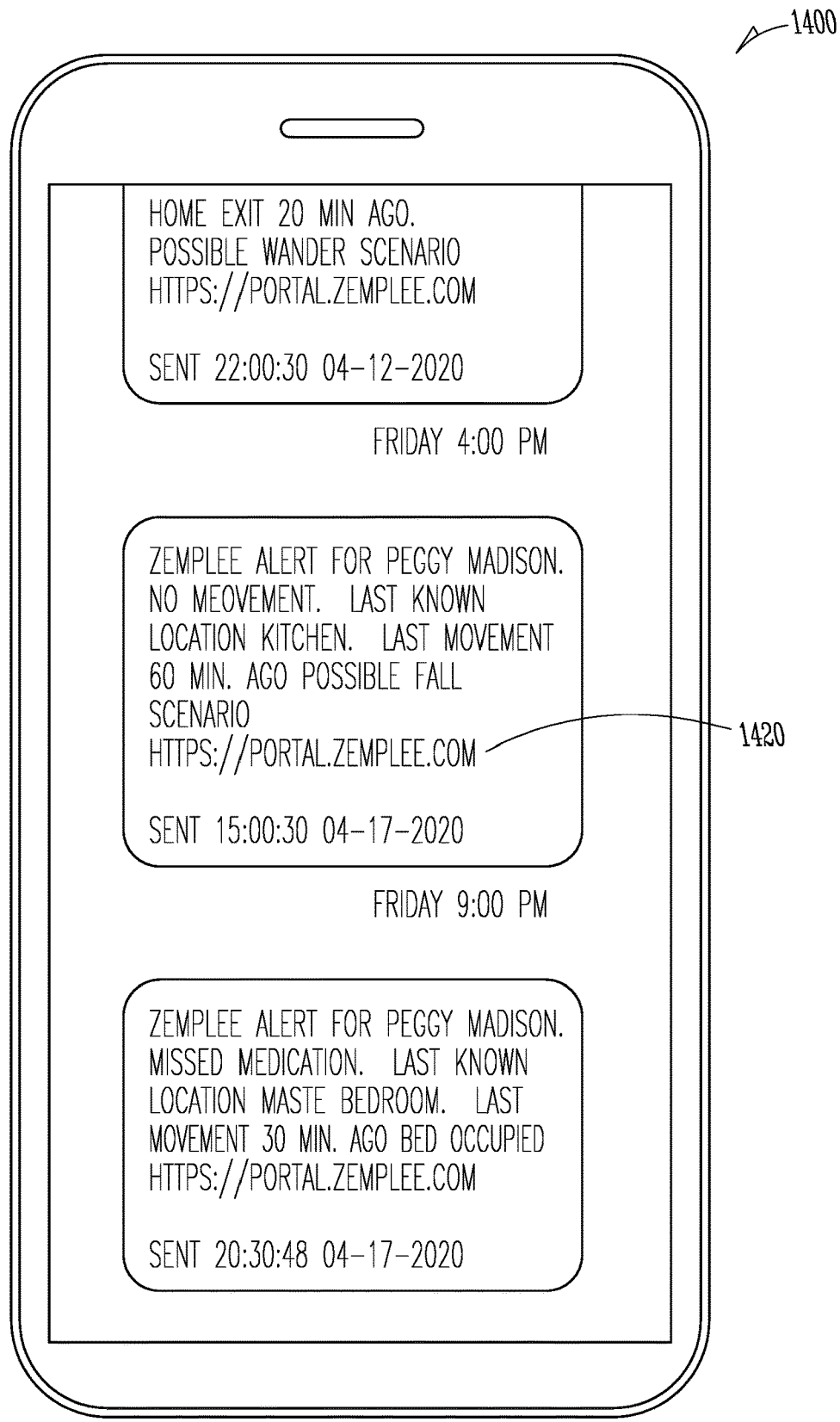
FIG. 15A is an illustrative drawing representing an example alert message displayed in care circle member's mobile phone or mobile application.

In response to a payor login type login type login to the application 129 at a third user device 132, computer instructions stored in a non-transitory memory and configure the device 128 to implement the third monitoring and control module $129_3$ to cause the sensor data processing and communication system 1200-2 to periodically send to a client application instance 131 at the third device 132, summaries, health profile, reports on the state health and well-being, trends indicating improvement or deterioration, aggregated data and analytics, which can be used for example, as inputs to further enrich and enhance risk stratification actuarial models, health profiles and actuarial processes. FIGS. 15A-

15B, 16A-16B, 17 and 18, which are explained in more detail below, are examples of alert information and periodic status information displayed at one or more of the devices 128, 130, and 132.

For example, a special-purpose computer system 2100 able to implement any one or more of the methodologies described herein is discussed below with respect to FIG. 21, and such a special-purpose computer accordingly can be a means for performing any one or more of the methodologies discussed herein. Within the technical field of such special-purpose computers, a special-purpose computer that has been specially modified (e.g., configured by special-purpose software) by the structures discussed herein to perform the functions discussed herein is technically improved compared to other special-purpose computers that lack the structures discussed herein or are otherwise unable to perform the functions discussed herein. Accordingly, a special-purpose machine configured according to the systems and methods discussed herein provides an improvement to the technology of similar special-purpose machines.

In various embodiments, one or more portions of the network 105 may be an ad hoc network, an intranet, an extranet, a virtual private network (VPN), a local area network (LAN), wireless LAN (WLAN), a wide area network (WAN), a wireless WAN (WWAN), a metropolitan area network (MAN), a portion of the Internet, a portion of the Public Switched Telephone Network (PSTN), a cellular telephone network, a wireless network, a Wi-Fi network, a WiMax network, a satellite network, a cable network, a broadcast network, another type of network, or a combination of two or more such networks. Information may be transmitted over 105 using a transmission medium via a network interface device (e.g., a network interface component included in the communication components) and utilizing any one of a number of well-known transfer protocols (e.g., HTTP). Any one or more portions of the network 105 may communicate information via a transmission or signal medium. As used herein, "transmission medium" refers to any intangible (e.g., transitory) medium that is capable of communicating (e.g., transmitting) instructions for execution by a machine (e.g., by one or more processors of such a machine), and includes digital or analog communication signals or other intangible media to facilitate communication of such software.

FIG. 2 is an illustrative drawing showing a top elevation view of a second example dwelling 200 in which multiple sensors 202-224 are located to sense health status and activity of a resident (not shown) of the dwelling 200. The dwelling 200 is bounded by outer walls 226, which encompass a dwelling interior that includes a region in which a resident can traverse by walking or with the aid of a wheelchair, for example, referred to as an "available ambulatory surface area" (AAS) 227. The example dwelling 200 includes inner walls 228 that segment the dwelling interior into multiple into multiple rooms. The example dwelling 200 includes an external access door 230 and internal doors 232. The rooms in the example dwelling 200 include balcony, kitchen and dining area, living area, bedroom, bathroom, and entry hall. Static objects located within the dwelling interior that overlay portions of the AAS 227 act as obstacles that can interrupt a president's movement within the example dwelling 200. In general, a resident's traversal path within the dwelling interior must circumvent static objects located between terminal points of such path. Example static objects include, Tables (T), Chairs (C), Kitchen Sink (KS) area, Bed (B), Toilet Seat (TS), and Bathroom Sink (BS) area.

The sensors 202-224 are located at the dwelling 200 to cooperatively track movement of a resident along one or more anticipated traversal paths (ATPs), discussed below with reference to FIGS. 3-4, between corresponding terminal points within the dwelling 200. Multiple terminal points 234-244 are identified within the dwelling 200. In an example monitoring system, the terminal points are located at static objects where it is expected that a resident's ambulatory movement along an ATP will begin and/or end. Multiple anticipated location of appearance points 246-254 such as the bedroom or bathroom are identified within the dwelling. One or more sensors are located within the dwelling 200 within sensing range of each anticipated location of appearance points.

Each ATP has at a minimum two terminal points. Both a point of origination of an ATP and a point of termination of the ATP are terminal points. An ATP may be bidirectional. In an example monitoring system, terminal points are located within a dwelling at locations where it is anticipated that a resident will transition from a static state to a mobile state. For example, it is well established that for the elderly, most accidents occur when transitioning from a static state to mobile state due to loss in balance. As explained more fully below, an example monitoring system uses one or more first sensors to sense when a resident is in ambulatory at a first terminal point of an ATP and uses one or more second sensors to senses when the resident is in motion at a second terminal point of the ATP. Sensing movement of the resident at the first terminal point of the ATP by the one or more first sensors initiates an ATP sensing event that causes monitoring of one or more second sensors to determine whether the one or more second sensors sense movement of the resident at the second terminal point of the ATP within a prescribed time interval. Sensing movement of the resident at the first terminal point of the ATP followed by sensing movement of the resident at the second terminal point within the prescribed time interval is indicative of the resident's having successfully traversed the ATP. However, sensing movement of the resident at the first terminal point of the ATP followed by no sensing of movement of the resident at the second terminal point of the ATP within the prescribed time interval, is indicative of the resident's having flailed to successfully traverse the ATP, which can trigger a safety alert. Once a resident successfully reaches the second terminal point, the sensing event ends. Continuing with this example, after a determination that the resident has successfully traversed the ATP for the first terminal point to the second terminal point, a new sensing event is initiated in response to the one or more second sensors sensing, that the residents is in ambulatory motion at the second terminal point. In an example monitoring system, sensors can be used to evaluate safety of a resident's movements in either direction along an ATP, from a first terminal point to a second terminal point and from a second terminal point to a first terminal point.

Figure 3:
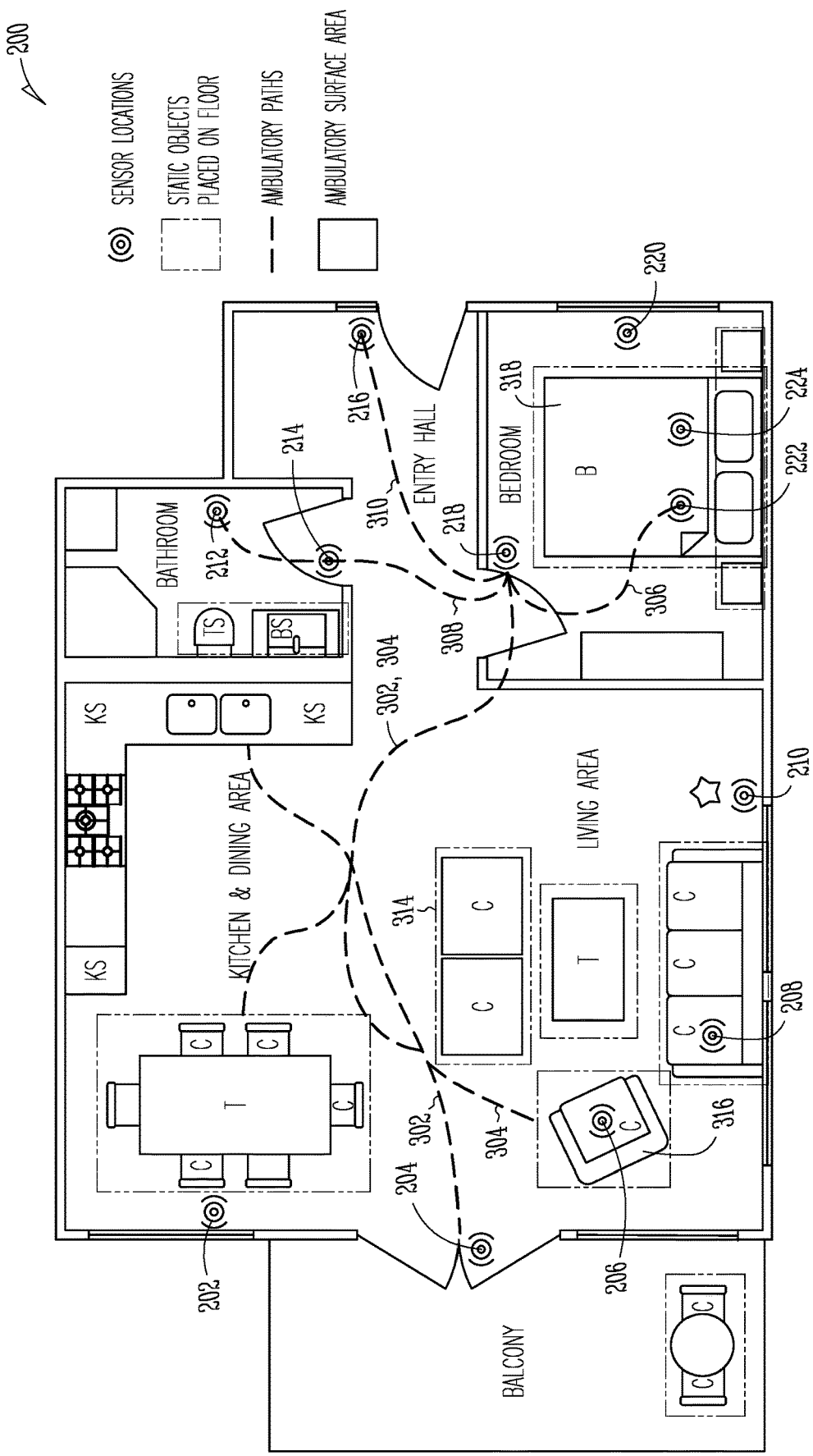
FIG. 3 is an illustrative drawing showing the top elevation view of the second example dwelling indicating multiple anticipated traversal paths (ATPs).

FIG. 3 is an illustrative drawing showing the top elevation view of the second example dwelling 200 indicating multiple example ATPs. The example ATPs are indicated by dashed lines. A first example ATP 302 extends between a door at the balcony to the inside bedroom. A sensor 204 that has a field of view that includes a passageway through the entry door at the balcony senses a resident's motion at a first terminal point of the first ATP 302, and a sensor 218 having a field of view that includes a doorway area just inside the bedroom senses a resident's motion at a second terminal point of the first AAP 302. It is noted that the first ATP 302 circumvents stationary object 314 (chairs). An example sensor 204 can be a motion type sensor. The sensor 218 can be a motion type sensor. A second example ATP 304 extends between a stationary chair 316 to the doorway area just the inside bedroom. A sensor 206 that has a field of view that includes the chair 316 senses a resident's motion at a first terminal point of the second ATP 304, and the sensor 218 having the field of view that includes the doorway area just inside the bedroom senses a resident's motion at a second terminal point of the second ATP 304. The sensor 206 can be a pressure sensor for sensing chair occupancy. The second ATP 304 also circumvents stationary object 314 (chairs). It is noted that the first and second ATPs 302, 304 overlap in a region between the kitchen/dining area and the bedroom. A third example ATP 308 extends between a left side of a stationary bed 318 a doorway at the inside of the bedroom. A sensor 222 that has a field of view that includes a left side of the bed 318 senses a resident's motion at a first terminal point of the third ATP 306, and the sensor 218 having the field of view that includes the area at the doorway just inside the bedroom senses a resident's motion at a second terminal point of the third ATP 306. The sensor 222 can be a pressure sensor for sensing bed occupancy. A fourth example ATP 308 extends between a doorway area just inside the bathroom and the doorway area just inside of the bedroom. A sensor 214 that has a field of view that includes the doorway area just inside the bathroom senses a resident's motion at a first terminal point of the fourth ATP 308, and the sensor 218 having the field of view that includes the area at the doorway just inside the bedroom senses a resident's motion at a second terminal point of the fourth AAP 308. The sensor 214 can be a motion sensor. A fifth example ATP 310 extends between a doorway area just inside to entry hall and the doorway area just inside of the bedroom. A sensor 216 that has a field of view that includes the doorway area just inside the entry hall senses a resident's motion at a first terminal point of the fifth ATP 310, and the sensor 218 having the field of view that includes the area at the doorway just inside the bedroom senses a resident's motion at a second terminal point of the fifth ATP 310. The sensor 216 can be a door open-close sensor.

Different ATPs can be associated with different levels of risk. For example, an ATP that includes traversal to or from a bath or shower can be more dangerous than an ATP that includes a traversal between hallway and kitchen. Moreover, ATPs can have different levels of risk at different times of day. For example, a chair or a sofa may have a lower risk factor compared to a bed during daytime, but the risk factor for both the chair and bed could be equal during night times. An example monitoring system can associate different risk factor weights with different terminal points and the risk factor weights can vary with time of day, for example.

FIG. 4 is an illustrative chart representing example identification and risk scoring of ATP terminal points. For each ATP, the chart indicates a starting (from) terminal point and ending terminal point (to), a time frame, a risk score and a legend describing the ATP. Referring to the third, fifth and sixth rows in the illustrative chart, for example, a person attempting to traverse a path from kitchen to bathroom during daytime has a lower risk score because it is assumed that such a person will be more physically or cognitively alert during daytime. Ambient conditions such as natural or artificial lighting improves visibility. In contrast, referring to the tenth through fifteenth rows, for example, a person attempting to traverse a path after exiting from a bed to a terminal point such as bathroom or kitchen in the night will have the highest risk score. An exit from a bed can be destabilizing and poor lighting conditions in the night can reduce visibility increased the risk of an accident or a fall incident or injury.

The sensors 202-224 are located within the dwelling 200 based at least in part upon ATPs between terminal points within the dwelling. ATPs can be defined based upon anticipated terminal points of a resident's ambulatory movements within the dwelling 200. ATPs can be defined initially at sensor installation time based at least in part upon locations of static objects, walk, and doors within the dwelling. ATPs within a dwelling can be adjusted over time based upon sensor measurements of actual movement of a resident within the dwelling. As explained more fully below, an example system uses machine learning techniques to learn ATPs based at least in part upon observation of actual ambulatory movement of residents within one or more dwellings.

More particularly, each sensor has a field of view and corresponding range. The multiple sensors within the dwelling 200 are located so that for each of one or more ATPs. A first terminal point of an example ATP and a second terminal point of the ATP are within the fields of view of different sensors that have different fields of view. Based upon determining that a sensor located to sense a resident's movement at one of a first and second terminal point of an ATP has sensed a person's movement and determining whether another sensor located to sense the resident's movement at the other of the first and second terminal point of the ATP senses movement of the resident within a prescribed time interval, the system can evaluate the safety status of the resident by determining whether the resident has successfully traversed the ATP.

An example monitoring system is used to prognosticate resident behavior based upon machine learning results indicating ATPs, path traversal frequency (PTF), and typical ambulatory pace (TAP). As explained below, in response to a movement or activity from the home inhabitant the monitoring system 1200 enters a supervisory mode, anticipating sensors to be activated at one or several locations. Special rules, such as a weightage factor or the velocity of movement are applied, if the terminal point is a wheelchair or other ambulatory equipment.

Figure 5A:
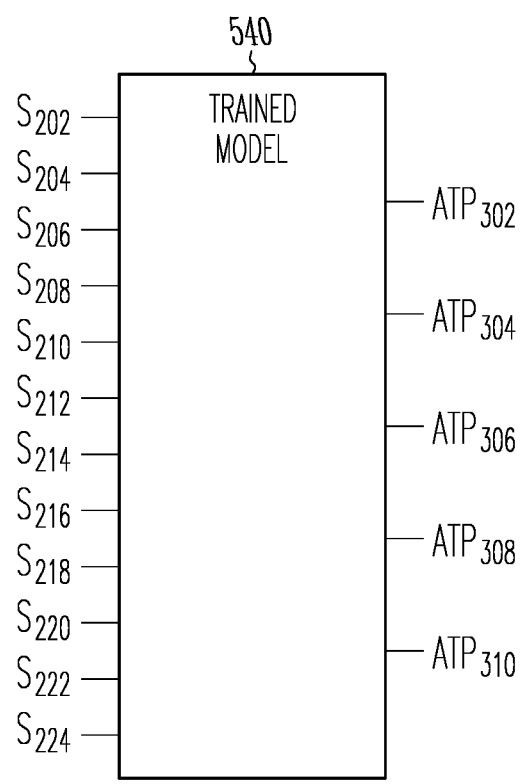
FIG. 5A is an illustrative drawing representing a trained model.
Figure 5B:
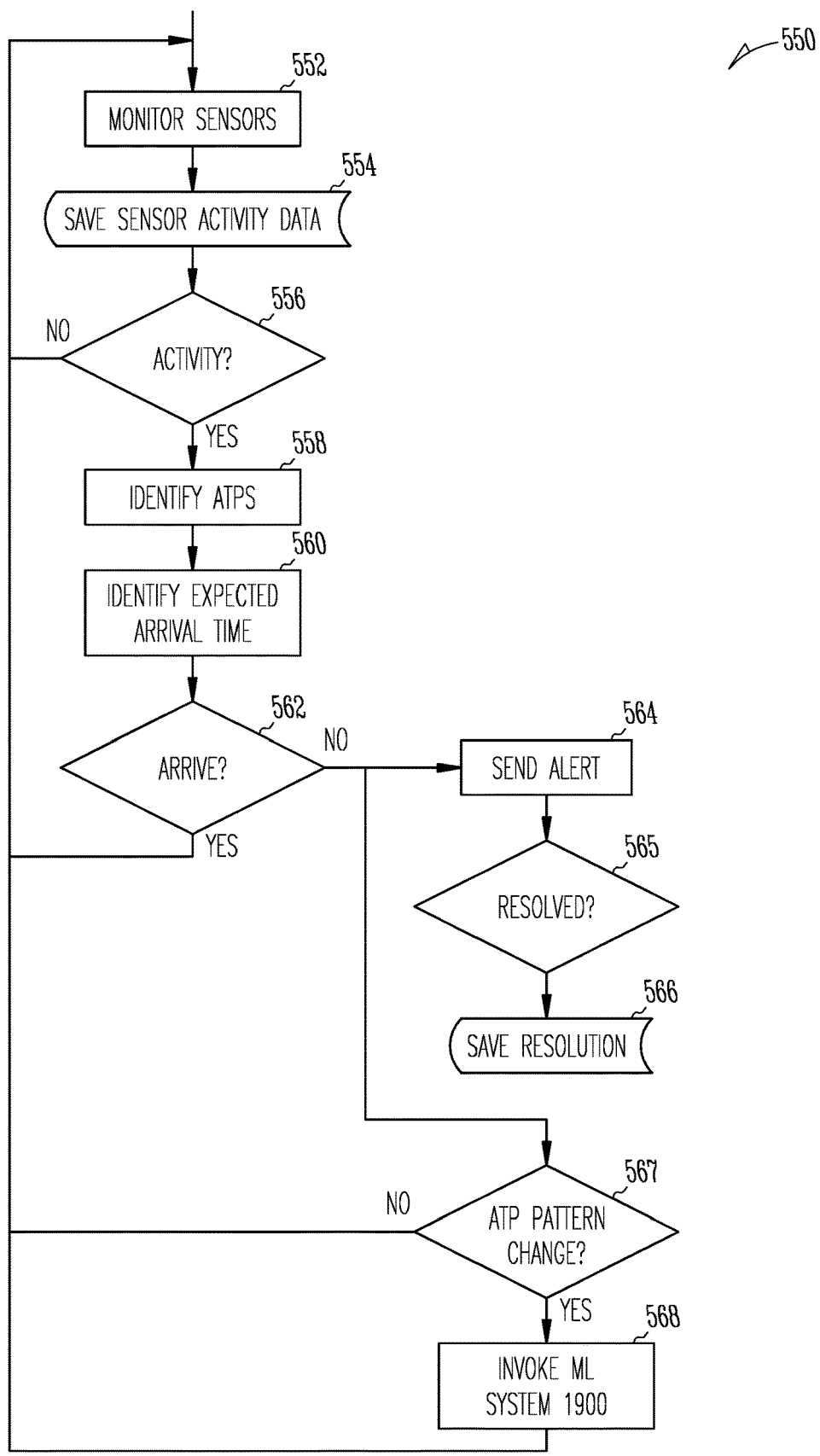
FIG. 5B is an illustrative flow diagram representing a first example ATP monitoring and parameter adjustment process to identify emergency risk events.
Figure 5C:
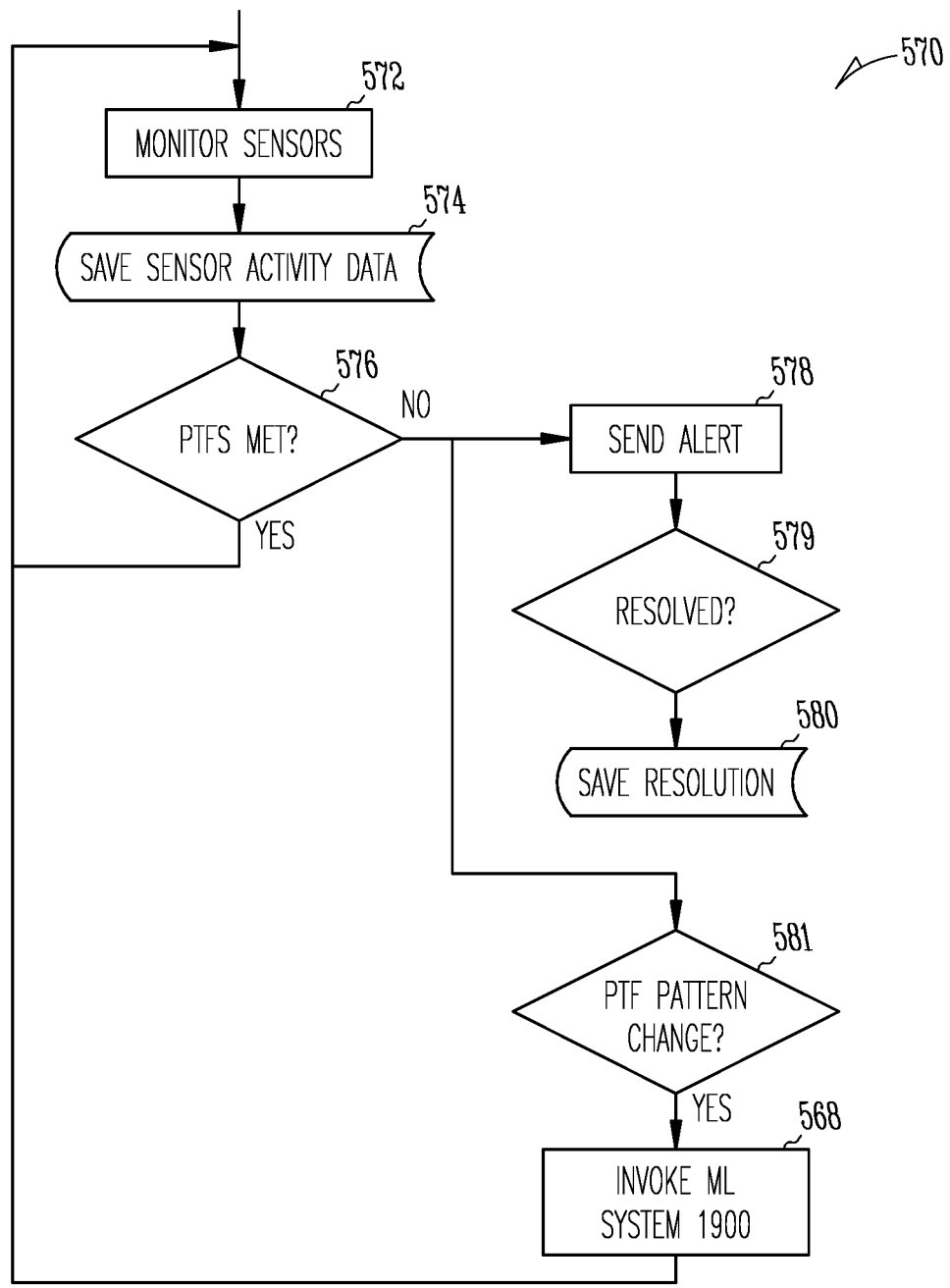
FIG. 5C is an illustrative flow diagram representing a second example ATP monitoring and parameter adjustment process to identify emergency risk events.
Figure 5D:
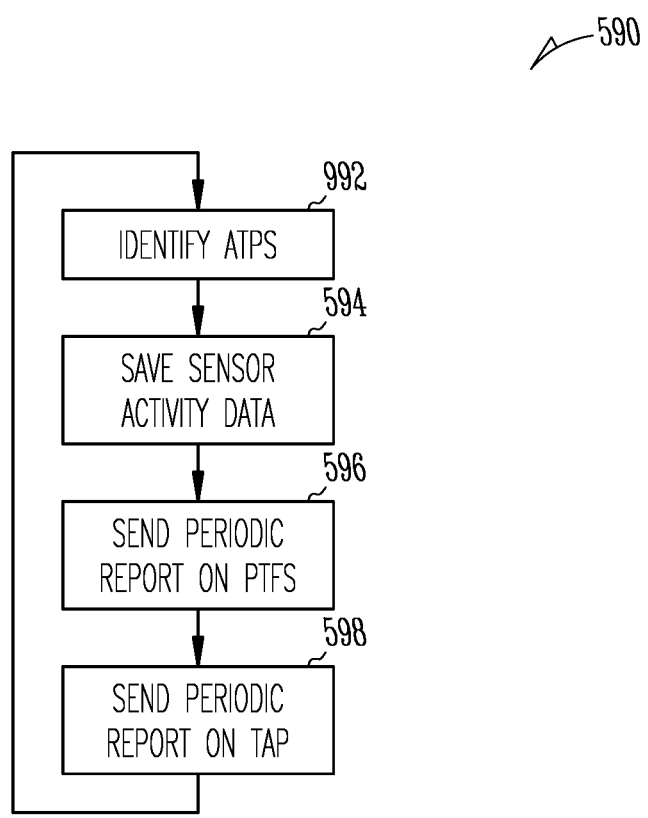
FIG. 5D is an illustrative flow diagram representing a third example ATP monitoring process to monitor long term risk.

FIG. 5A is an illustrative drawing representing a trained model 540 trained using an example machine learning (ML) engine 1900 described more fully below with reference to FIG. 20. The trained model 540 uses as input sensor measurement values $S_{202}$-$S_{224}$ representing measurements of a resident's activity detected at one or more of sensors 202-224 to infer resident activity at one or more of ATPs 302-310 indicated using output values $ATP_{302}$-$ATP_{310}$. FIG. 5B and FIG. 5C, illustrate example processes used to send alerts and adjust parameters for determining alerts that are triggered using the trained ML model 540, based resident activity detecting using the sensors. FIG. 5D) illustrates example process used to send periodic updates of resident's health status based resident activity detecting using the sensors.

FIG. 5B is an illustrative flow diagram representing a first example ATP monitoring and parameter adjustment process 550 to identify emergency risk events, One or more computing machines 2100 that implement the sensor data processing and communication system 1200-2, are configured using executable instructions stored in a non-transitory memory device that when executed, cause processor circuitry to perform one or more of the operations of the process AA00. The first ATP monitoring process 550 is described with reference to the example ATPs of FIG. 3 sensors system 1200-1 of FIG. 1A. However, it will be understood that the process 550 can be performed with different arrangements and combinations of sensors and ATPs. Operation 552 continually accesses sensor measurement data of the multiple example sensors 202-224 to detect resident activity at the individual locations of the sensors. More particularly, an example operation 552 continually accesses sensor data to determine whether any of them detect resident activity. An example operation 552 continually accesses sensor measurement data by polling sensor memory $101_3$ that stores data for of each of sensors 202-224, at periodic time intervals for stored data indicating occurrence and time of occurrence of sensed resident activity. Polling frequency can be set in individual sensors or in a rules management operation 418 described below, for example. Alternatively, operation 552 may continually access sensor measurement data by receiving data pushed at periodic time intervals over the network 105 to the system 1200-2. Operation 554 stores sensor data over a time interval long enough to determine whether a resident's actual path traversal frequency for one or more ATPs has deviated sufficiently from the resident's PTFs for the ATPs to trigger an emergency alert. The stored sensor data includes indicia of time of occurrence, which may include sequencing of saved sensor data based upon time at which sensor data is captured at the sensor and may include time stamps as to time of day and say of week at which the sensor data was produced at the sensors, for example. Decision operation 556 evaluates information obtained from the sensors multiple time intervals to determine whether sensor data indicates that one or more sensors has sensed resident activity. On a condition that decision operation 556 determines that the sensor data indicates no detection of resident activity, control returns to operation 552. On a condition decision operation 556 determines that sensor data indicates that one or more sensors sensed resident activity, operation 558 identifies one or more ATPs based upon the model 540 of FIG. 5B, determined using a trained ML model, associated with sensors for which activity is sensed. As explained above, each ATP 302-310 includes a first end point and a second end point. As explained below, in an example monitoring system, 1200, ATPs can be determined based upon trained ML models. Operation 560 identifies expected traversal times for ATPs identified in operation 558. As explained below, an example resident can have a typical ambulatory pace (TAP) and ATPs within a residence can have a Mean Distance between End Points (MDEP). In an example monitoring system, TAP and MDEP can be determined based upon trained ML models. An example operation 560 determines expected traversal times for the identified paths based upon the TAP and the MDEP. Alternatively, an example operation 560 can determine expected traversal times for individual paths through empirical measurement of resident's actual time to complete each ATP.

Decision operation 562 determines whether the sensor data indicates that the resident has completed traversal of one of the ATPs identified at operation 558 within the expected traversal time determined in operation 560. The expected traversal time can be a predetermined time interval learned using the trained machine learning model based upon range of times in which a resident typically completes traversal of an ATP. The predetermined time interval can be determined based upon calculation of standard deviation of ATP traversal times, for example. On a condition that decision operation 562 determines that sensor data indicates that the resident has completed at least one path, control is returned to operation 552. On a condition that decision operation 562 determines that the sensor data indicates that a resident has completed traversal of NONE of the ATPs identified at operation 558, operation 562 causes operation 564 to cause the sending of an emergency alert event messages to user devices 128, 130 indicating an occurrence of a failed ATP traversal event, for example.

Decision operation 565 determines whether there is a successful resolution of the alert such as through action of a member of the resident's care circle's and if yes, saves alert resolution information 566 indicating information concerning the alert such as general condition of the resident, validity of the alert—for example—if the alert reported was a fall incident, the resolution would confirm it as a fall, for example. In an example system 1200, a care circle member uses a device (e.g., 128, 130, 132) to send a message indicating successful ATP traversal. A successful resolution provides an indication that the failed ATP traversal may have been due to a change in resident behavior (e.g., the resident followed a different path) rather than due to an actual emergency. Also, on a condition that decision operation 562 determines that the sensor data indicates that a resident has completed traversal of NONE of the ATPs identified at operation 558, operation 562 causes decision operation 567 to determine, based upon historical sensor activity information saved at operation 554, whether there exists a pattern of occurrences of non-completions of the one or more ATPs identified in operation 558 within corresponding arrival times identified in operation 560 that suggest the non-completions represent a possible change in resident behavior instead of emergency events. The resident's following a different path may indicate new resident ATP behavior. The alert resolution information 566 can contribute to the determination of patterns by indicating if the AI's deduction of the adverse scenario for which the alert was generated is accurate or a false positive, for example. On a condition that decision operation 567 determines that the there is no such pattern indicating a change in resident behavior, control returns to operation 552. On a condition that decision operation 567 determines that there is a pattern indicating a change in resident behavior pattern, operation 567 triggers actuation of ML operation 568 to cause retraining the model 540, which can involve updating of one or more of TOD, DOW, ATP and PTF used in training the model 540. Control then flows back to operation 552.

FIG. 5C is an illustrative flow diagram representing a second example ATP monitoring and parameter adjustment process 570 to identify emergency risk events, One or more computing machines 2100 that implement the sensor data processing and communication system 1200-2, are configured using executable instructions stored in a non-transitory memory device that when executed, cause processor circuitry to perform one or more of the operations of the process BB00. Operation 572 continually accesses the sensor measurement data of the multiple example sensors 202-224 to detect resident activity at the individual locations of the sensors, More particularly, an example operation 572 continually accesses sensor data to determine whether any of them detect resident activity. An example operation 572 continually accesses sensor data by polling sensor memory $101_3$ that stores data for each of sensors 202-224 at periodic time intervals for stored data indicating occurrence and time of occurrence of sensed resident activity. Polling frequency can be set in individual sensors or in a rules management operation 418 described below depending on the user and sensor data rules, for example every 3 seconds, for example. Alternatively, operation 572 may continually accesses sensor data by receiving data pushed over the network 105 at periodic time intervals to the system 1200-2. Operation 574 stores sensor data over a sensor inactivity time interval, set using the rules management operation 418, that is long enough to determine whether a resident's actual path traversal frequency for one or more ATPs has deviated sufficiently from the resident's PTFs for the ATPs to trigger an emergency alert. The stored sensor data includes indicia of time of occurrence, which may include sequencing of saved sensor data based upon time at which sensor data is captured at the sensor and may include time stamps as to time of day and say of week at which the sensor data was produced at the sensors, for example. Decision operation 576 evaluates information obtained from the sensors to over multiple time intervals to determine whether sensor data indicates that path traversal frequencies (PTFs) determined using a trained ML model for one or more ATPs indicates a possible occurrence of a risk event. More particularly, decision operation 576 determines whether the sensor data indicates a change in frequency with which the resident traverses an ATP that suggest that the resident may have suffered a medical event or be in distress. An expected predetermined PTF range can be learned using the trained machine learning model based upon range of frequencies in which a resident typically traverses an ATP. A predetermined Range of PTFs can be determined based upon calculation of standard deviation of PTFs, for example. For example, a resident may traverse an ATP between 2-17 times per week with 10 times per week being the mean and 3 being the standard deviation. On a condition that decision operation 576 determines a deviation from expected PTF that is outside a predetermined range, which can be set using rules operation 418, operation 578 causes the sending of an emergency alert event messages to user devices 128, 130 indicating an occurrence of a failed PTF event, for example. Decision operation 579 determines whether there is a successful resolution of the alert such as through action of a member of the resident's care circle's and if yes, saves alert resolution information 580 indicating information concerning the alert such as general condition of the resident, validity of the alert—for example if the alert reported was a fall incident, the resolution would confirm it as a fall, for example. In an example system 1200, a care circle member uses a device (e.g., 128, 130, 132) to send a message indicating that the resident traversed a different ATP, for example. A successful resolution provides an indication that the failed FTP may have been due to a change in resident behavior (e.g., the resident followed a different path or has begun following the same ATP at a different frequency) rather than due to an actual emergency. Also, on a condition that decision operation 576 determines a deviation from expected PTF that is outside a predetermined range, decision operation 581 determines, based upon historical sensor activity information saved at operation 574, whether there exists a pattern of PTFs deviations indicated in the sensor activity data saved at operation 574 that suggests that the deviating PTFs represent a possible change in resident behavior pattern instead of emergency events. The resident's activity at a different frequency or on different paths may indicate new resident ATP behavior. The alert resolution information 566 can contribute to the determination of patterns by indicating whether the AI's deduction of the adverse scenario for which the alert was generated is accurate or a false positive for example. On a condition that decision operation 581 determines that the there is no such pattern indicating a change in resident PTF behavior, control returns to operation 572. On a condition that decision operation 581 determines that there is a pattern indicating a change in resident PTF behavior pattern, operation 581 triggers actuation of ML operation 568 to cause retraining the model 540, which can involve updating of one or more of TOD, DOW, ATP and PTF used in training the model 540. Control then flows back to operation 572.

Referring to FIG. 5C and to FIG. 4, for example. The DOW column in the chart in FIG. 4 indicates PTFs for different ATPs by day of week. The chart indicates for an ATP with terminal points C145-64301964 and C145-02345675 has an expected PTF of 5 on Thursday and indicates that an ATP with terminal points C145-02345676. And C145-64301964 has an expected PTF of 5 on Thursday. For example, on a condition that operation 576 determines that the sensor data saved at operation 574 indicate no path traversals on either of those ATPs on Thursday, then an example operation 576 causes operation 578 to cause the sending of an emergency alert event messages to user devices 128, 130 indicating an occurrence of an emergency event. Also, on a condition that decision operation 576 determines that the sensor data indicates that a resident has not completed any path traversals on either of those ATPs on Thursday, then an example operation 576 causes decision operation 580 to determine, based upon historical sensor activity information saved at operation 574, whether there exists a pattern of PTF on the ATPs identified in the example chart of FIG. 4 that suggest the non-compliant PTFs represent a possible change in resident behavior instead of emergency events. On a condition that decision operation 580 determines that the there is no such pattern indicating a change in resident behavior, control returns to operation 572, On a condition that decision operation 580 determines that there is a pattern indicating a change in resident PTF behavior, operation 580 triggers actuation of ML operation 568 to update one or more of TOD, DOW, ATP and PTF for one or more of the PITS evaluated at decision operation 576. Control then flows back to operation 572.

Still referring to FIG. 5C, consider for example that a resident, Mrs. Smith, has been in the habit of waking up at 6:00 AM every morning. A sensor such as a pressure sensor can be located at Mrs. Smith's bed or a motion sensor can be located in range of Mrs. Smith's bed to sense each day whether Mrs. Smith is awake. The rules operation 418 can be setup with an alert rule to cause decision operation 576 to cause operation 578 to send an alert at 8:00 AM if sensor measurements indicate that Mrs. Smith is not awake by 8:00 AM. This is to notify members of Mrs. Smith's care circle on the off-chance case that Mrs. Smith passed away in her sleep, for example. The alert is an "open" state until it is closed by a member of Mrs. Smith's care circle or if subsequent activity by Mrs. Smith is detected in the house. Suppose for example that on a given day, Mrs. Smith awakens at 8:30 AM and starts and moved around the house. The pressure sensor or the motion sensor located nearby her be would sense that she is awake. The alert will resolve and set the alert status will be reset to "She is OK". The alert resolution Assume for example that this was a singular incident—happened to be the first one. So, decision operation 580 determines that there is no pattern change to trigger the activate ML operation 568. However, suppose for example, that Mrs. Smith has awakened at 8:00 AM for the last 30 days. If the rules were not changed—the system would continue to send an alert out saying she has passed away, the alert being a false alert every day. Decision operation 580 would recognize the changed pattern in which Mrs. Smith has consistently been waking up at 8:00 AM and would trigger the activate ML operation 568. An example ML training operation 2100, goes back into historical data for the past 90 days (regression analysis), for example, check for other events (e.g., in the API)—perhaps Mrs. Smith had a hospitalization event? Or a change in medication (data from EHR). If the regression indicates a permanent change—e.g., Mrs. Smith has been waking up at 8:00 AM for the past 7/10 days, for example, then ML training adjusts one or more of the TOD, DOW, ATP and PTF and a training data set is adjusted in such a way that the new time 8:00 AM is now the rule.

FIG. 5D is an illustrative flow diagram representing a third example ATP monitoring process 590 to monitor long term risk. One or more computing machines 2100 are configured using executable instructions stored in a non-transitory memory device that when executed, cause processor circuitry to perform one or more of the operations of the process 590. Operation 592 monitors the multiple example sensors 202-224 to determine whether any of them detect resident activity. An example operation 592 periodically polls sensor memory of each of sensors 202-224 for stored data indicating occurrence and time of occurrence of sensed resident activity. Operation 592 stores sensor data over a time interval that is long enough to identify changes in path traversal activity that may be indicative of decline in health or wellbeing, such as over a period of 90 days. More specifically, an example operation 594 stores sensor data over a time interval long enough to capture changes in a resident's PTF or in a resident's TAP, determined using trained ML model, that indicate possible decline in health or wellbeing. Operation 596 produces periodic reports of a resident's PTFs for different ATPs over time. Operation 598 produces periodic reports of a resident's TAP over time. Changes in PTFs and changes in TAP can be indicative of decline in the health or wellbeing of the resident. For example, less frequent path traversals and slower TAP can be indicative of decline, such as, if the patient is recovering post hospitalization from a hip fracture surgery which could reduce the activity level of the resident.

Figure 6A:
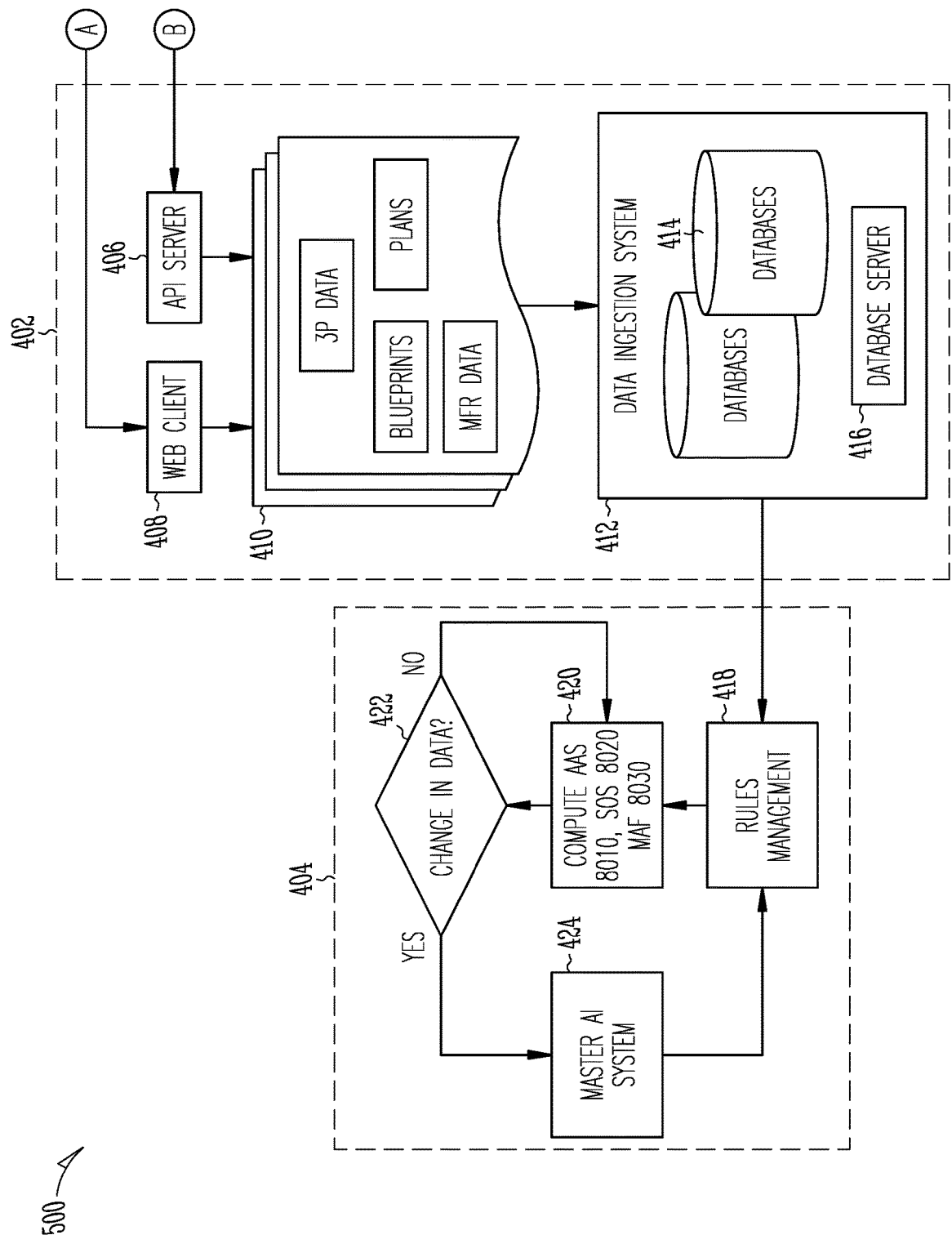
FIGS. 6A-6B are illustrative drawings representing computing system to compute information about ambulatory regions of a dwelling.
Figure 6B:
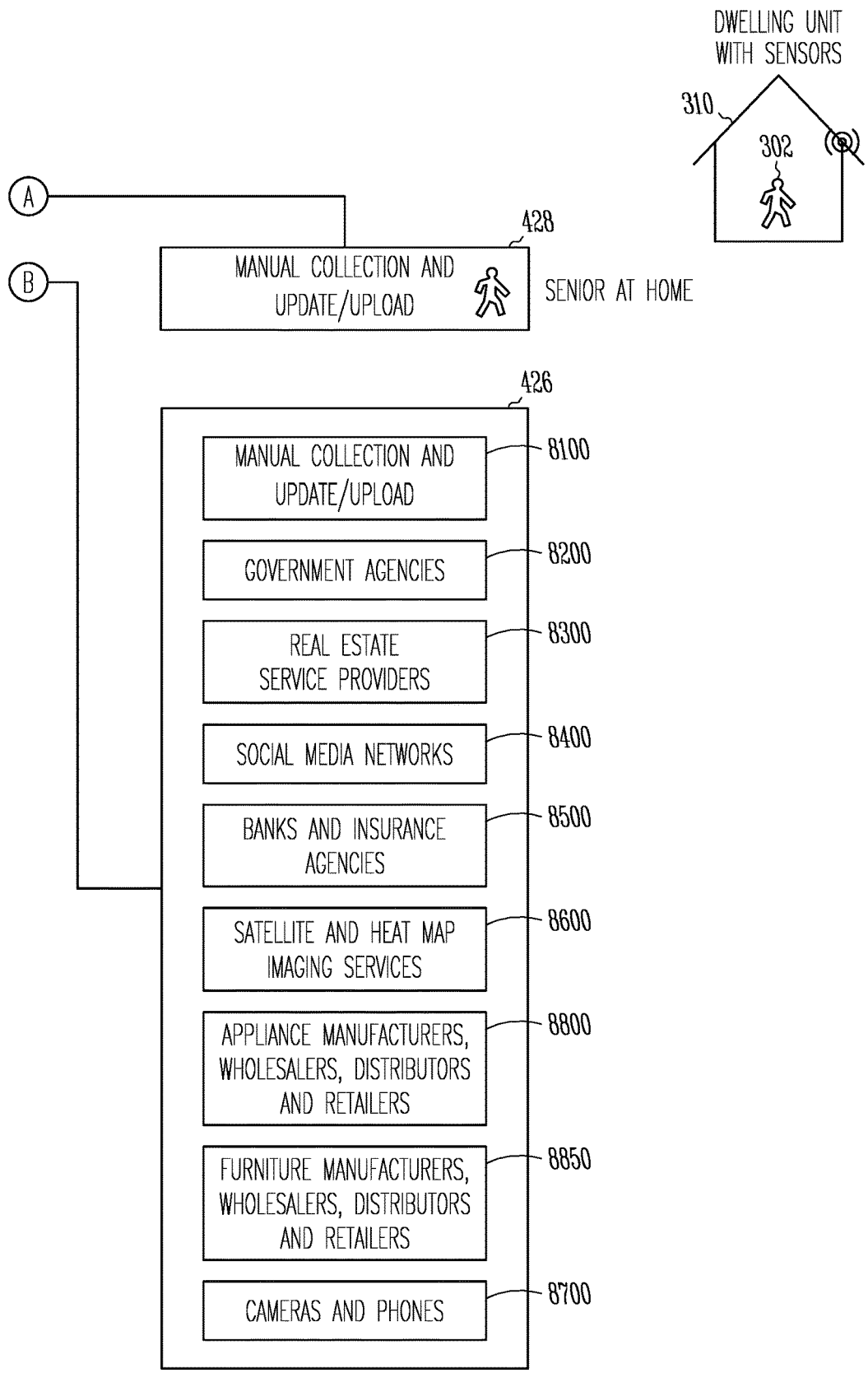

FIGS. 6A-6B are illustrative drawings representing computing system 400 to compute information about ambulatory regions of a dwelling, which can be used to determine parameters for placement locations of motion sensors and ATPs, for example. The ambulatory area computing system 400 includes a surface area data collection system 402 and an ambulatory field computation system 404. The data collection system 402 and the ambulatory field computation system 404 are implemented using one or more computing machines programmed with executable instructions stored in a non-transitory to perform the operations 418-424 described below. The data collection system 402 includes an API (application program interface) server 406 and a web client 408 that are coupled to receive information over a network and to provide the information to a residential structure data collection and aggregation server 410, which maintains a repository of the data on the structure of the home. The residential structure data collection and aggregation server 410 provides the received information to a data ingestion system 412, which includes a database storage memory 414 to store information such as dimensions of the home or room, dimensions of the appliances and furniture and includes one or more database servers 416 to control inputting and outputting of the stored information.

In an example monitoring system, dwelling area information is collected indicating dwelling surface area and dwelling layout can be provided over the network 105. Information indicating dwelling dimensions can be collected manually by care giver service personnel 428 who measure dimensions of a dwelling and use a computing device (not shown) to send the dimensions over the network 105 via the web client 408. Alternatively, information indicating dwelling dimensions can be collected over the network 105 from third party public sources ("3P Data") 426 via the API server 406. Example 3P Data 426 can include floor plans, blueprints, images and other specifications of the home collectively to as 3P Data images of the dwellings served from websites of public domain repositories and property records 8100, government agencies 8200, Real Estate Service Providers 8300. Social Media Applications 8400, Banks and Insurance Agencies 8500, Satellite, Visual Imaging and Thermal or Heatmap Imaging Services 8600, and photographs or other visual imagery collected from devices such a cameras and smart phones 8700. The data may include details such as dimensions of a room, dimensions of different living areas of the dwelling, dimensions of static objects such as furniture located in the dwelling, and total area of home and property, and dwelling unit area.

In an example monitoring system, static object area information is collected indicating static object dimensions can be provided manually by care giver service personnel 428 who measure dimensions of a dwelling and use a computing device (not shown) to send the dimensions over the network 105 via the web client 408. Alternatively, information indicating static object dimensions can be obtained over the network 105 from third party public sources ("3P Data") 426 via the API server 406. Example 3P Data 426 can include generally available data sources from appliance manufacturers, wholesalers, distributors, and retailers 8800 and furniture manufacturers, wholesalers, distributors, and retailers 8850. Static objects may include dining table, furniture, appliances, piano and more, for example.

The collected data is provided to the ambulatory field computation system 404. A rules management operation 418 receives the collected data, performs positioning, computing the surface area and volume and mapping. The rules management operation 418 provides an estimate of usable surface area to an ambulatory field computation operation 420. For each of n floors of a dwelling, the ambulatory field computation operation 420 computes a maximum ambulatory field (MAP) in which a resident can move about, based at least in part upon an available ambulatory surface (AAS) and a static object surface area (SOS) according to the following relationship.

$$MAF = \sum_{k=1}^{n}(AAS - SOS)$$

MAF=Maximum Ambulatory Field
AAS=Available Ambulatory Surface Area
SOS=Static Object Surface Area
n=Number of floors in a dwelling.

The ambulatory field computation operation 420 uses collected dwelling area information to determine AAS within a dwelling and uses the collected static object information to determine a total SOS within the dwelling. The ambulatory field computation operation 420 determines the MAF for a floor of a dwelling based upon a difference between an AAS of the floor of the dwelling and the SOS of the floor of the dwelling.

Figure 7:
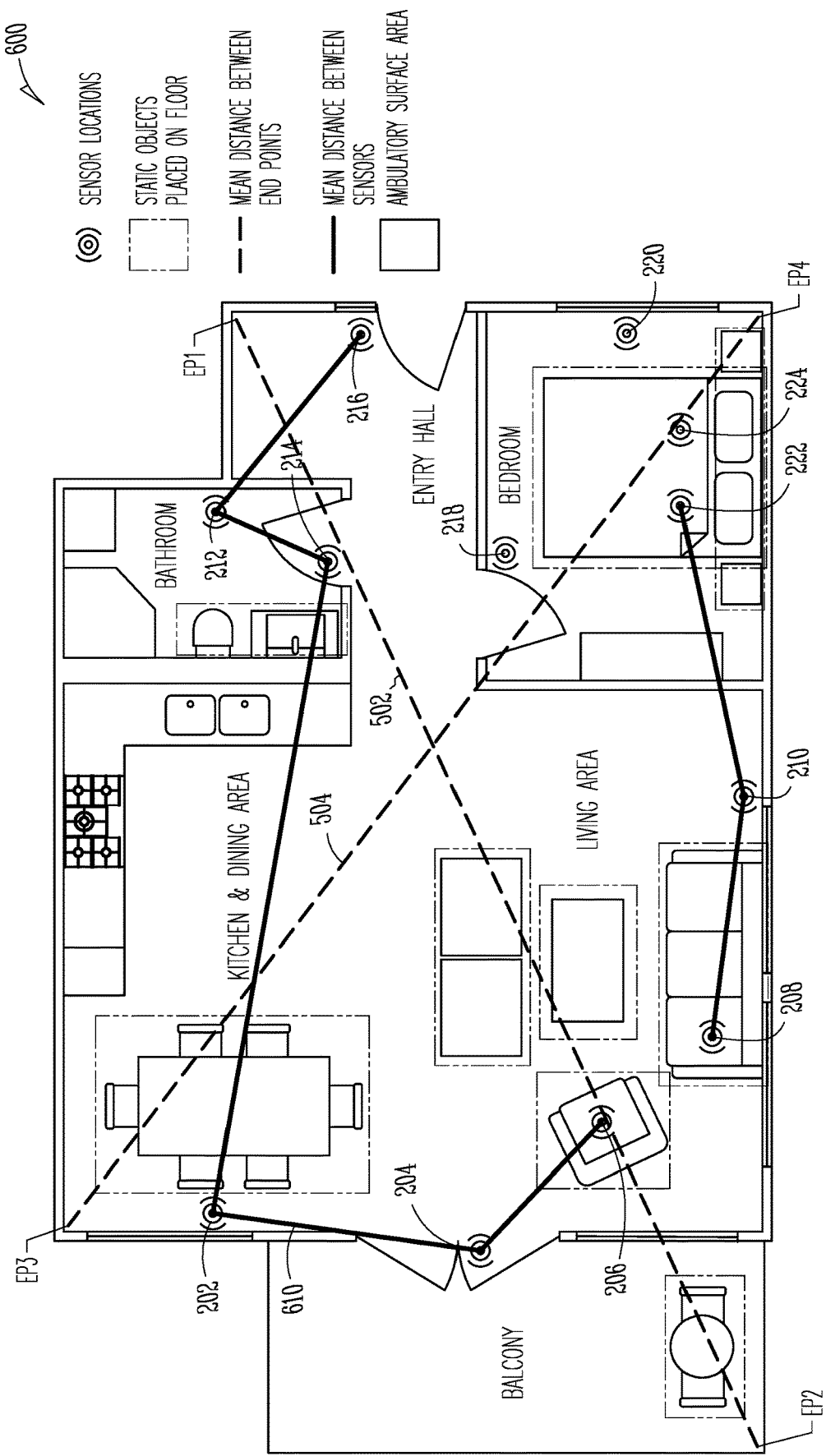
FIG. 7 is an illustrative drawing showing a top elevation view of the second example dwelling in which multiple sensors are located and indicating mean distances between endpoints and mean distances between sensors.

FIG. 7 is an illustrative drawing showing a top elevation view of the second example dwelling 200 in which multiple sensors 202-224 are located and indicating mean distances (MDEP) between endpoints and mean distances between sensors. As used herein, "end points" refer to diagonal points of the furthermost locations on a floor in a dwelling unit such as a home or apartment. First and second end points, EP1 and EP2, have the largest spacing between them on a first line 502 that extends between diagonally opposed corners of the example dwelling 200. Third and fourth end points, EP3 and EP4, have the largest spacing between them on a second line 504 that extends between diagonally opposed corners of the example dwelling 200. The length of the first line 502 represents the MDEP for EP1 and EP2, and the length of the second line 504 represents the MDEP for EP3 and EP4. In multi-storied homes, MDEP is also measured at one or more of top to down, vertically, and diagonally from furthermost points.

Referring again to FIGS. 6A-6B, an example ambulatory field computation operation 420 uses common mathematical and geometrical rules to determine one or more MDEPs in each floor of a dwelling based upon the collected dwelling area information. The MDEPs are used to determine the quantity of sensors needed to sufficiently provide supervisory area. This is necessary not only to ensure optimal coverage of sensing areas but also eliminate blind spots depending on the sensor's sensory range. The larger the distance MDEPs the more sensors are required between end points. In addition, the MDEP values are used to establish boundary conditions for movements within a home or an apartment. The ratio of MAF to the sensory range of the sensors is used to determine the placement locations of motion sensors.

A mean distance between sensors in the dwelling is determined based upon measurement of distance between the motion sensors, relative to the dimensions of the residence, Information indicating locations of sensor units within a dwelling unit and the mean distance between sensor units within the dwelling unit are stored in a memory device in association with information identifying the dwelling unit. The sensor location information and mean distance between sensors information are used together with ambulatory pace information, described below, to determine whether a resident who departs a first terminal point of an ATP reaches a second terminal point of the ATP within a prescribed time interval.

Still referring to FIGS. 6A-6B, the ambulatory field computation operation 420 provides any modifications such as relocation of certain furniture for example to a change in data operation 422, which. On a condition that there is no change in data ("no" branch), the change in data operation sends a signal to the ambulatory field computation operation 420 to cause to sustain the MAF and AAS. On a condition that there is a change in data ("yes" branch), the change in data operation 422 sends a signal to the Master AI (artificial intelligence) operation 424 to cause a recompute of the MAF and AAS. The AI operation 424, in turn, sends information to the ambulatory field computation operation 420 to cause to cause operation 420 to utilize the new information in calculating the MDEP.

Figure 8:
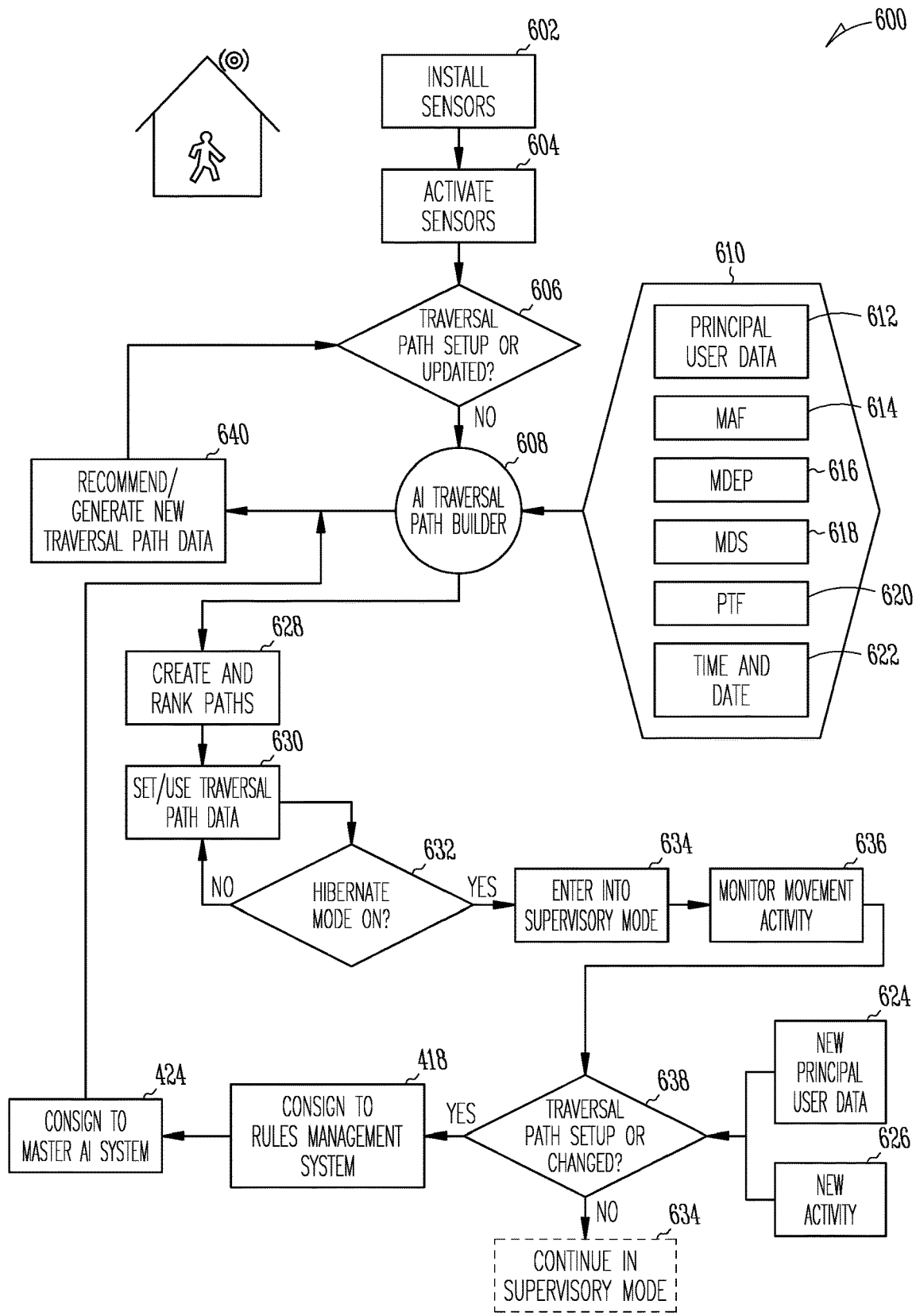
FIG. 8 is an illustrative flow diagram of a process to create and rank ATPs.

FIG. 8 is an illustrative flow diagram of a process 600 to create and rank anticipated traversal paths (ATPs). The ATPs, in turn, are used to train the model 540. One or more computing machines 2100 are configured using executable instructions stored in a non-transitory memory device that when executed, cause processor circuitry to perform one or more of the operations of the process 600. The process 600 of FIG. 8 shows additional example details of an example decision operation 567 of FIG. 5B. As used herein, ATPs refer to paths that a resident undertakes as part of normal activity. Operation 602 involves a technician installing multiple sensors within a dwelling at locations determined as described above. Operation 604 activates the sensors. At operation 606, baseline ATP information can be provided by a technician or a care giver at sensor setup time to det up a resident's ATPs. More particularly, in an exampling monitoring system, information about a resident's ATPs within a dwelling is often collected through a survey process conducted by care giver service personnel 428 using the web client 408 as described above with reference to FIGS. 6A-6B, at the time of equipping the home with sensors.

In scenarios where a resident is unable to articulate an ATP due to medical indisposition or is cognitively challenged, a baseline assumption can be made on the possible ATPs and a set of anticipated ATPs are assigned based upon behavior, most observed and familiar patterns that are common in other dwellings. For example, a first ATP can be assigned to extend between Bedroom and Living Room (e.g., a sensor located at the bedroom is designated as a first terminal point of the first ATP and a sensor located at the living room is designated as a second terminal point of the first ATP). An example second ATP can be assigned to extend between Bedroom and Bathroom (e.g., a sensor located at the bedroom is designated as a first terminal point of the second ATP and a sensor located at the bathroom is designated as a second terminal point of the second ATP). An example third ATP can be assigned to extend between Kitchen and Bedroom (e.g., a sensor located at the kitchen is designated as a first terminal point of the third ATP and a sensor located at the bedroom is designated as a second terminal point of the third ATP). An example fourth ATP can be assigned to extend between Entryway and Living room (e.g., a sensor located at the entryway is designated as a first terminal point of the fourth ATP and a sensor located at the living room is designated as a second terminal point of the fourth ATP). Additional ATPs can be assigned, based on the number of rooms or different areas in a dwelling—for example a solarium in the backyard or a lounging area in the balcony.

An AI ATP builder operation 608 builds ATPs. In an example monitoring system 1200, operation 608 builds an initial set of ATPs based upon the baseline ATP information provided during setup. An example AI ATP builder operation 608 receives runtime data 610 that can include principal user data, which can include information about the seniors use of ambulatory assistive aids such as walker, walking stick, wheelchair or human assistance. Example runtime data includes a dwelling's MAF 614, a dwelling's MINT 616, a dwelling's sensors' MDS 618, path frequency traversal (PTF) information 620 for ATPs within the dwelling to the dwelling, and time and date information 622 associated with ATPs. The principal user data 612 can be changed at operation 624, based upon technician or care giver updates concerning a resident. The PTF information 620 and the time and date information 622 can be updated at operation 626 based upon monitoring sensors to detect monitored patient activity.

The AI ATP builder operation 608 causes operation 628 to create and rank ATPs such as by assigning a numerical value based on importance and frequency of use. More specifically, operation 628 configures a computing system to associate sensors with ATP terminal points. The AI ATP builder operation also causes operation 630 to set/use ATP data. More particularly, operation 630 configures a computing system to associate date and time information and certain runtime information 610 such as PTF information and principal user information with the ATPs, and more particularly, with the sensors associated with the ATPs.

Operation 632 checks whether hibernate mode is active. Hibernate mode can be setup manually by the user or a caregiver or automatically when no activity or movement is detected in the dwelling for a certain number of days based as configured in the user settings. During the hibernate more there is no active monitoring. However, periodic checks will be done for maintenance. The hibernate mode is a mode in which the AI is set to expect no data for a hibernate time interval period. Operation 634 causes the monitoring system to enter a supervisory mode in response to a sensor sensing movement activity at a location associated with a first terminal point of an ATP created at operation 628. Operation 636 monitors sensors associated with the ATP to determine whether subsequent movement activity is detected within a prescribed time interval at a sensor at a location associated by operation 628 with second terminal point of the ATP. As explained more above, failure to detect monitored activity within the prescribed time interval can result in a notification being sent over the network 105 to monitoring personnel and/or family. As explained above, a single location can be a terminal point for multiple ATPS, and therefore, detection of activity at a sensor location by operations 634 can result in operation 636 monitoring for subsequent movement activity at multiple sensors, each associated with a terminal point of a different ATP.

Operation 638 determines whether there is a changed ATP. In an example monitoring system, operation 638 can detect a changed ATP based upon operation 636 determining that a sensor other than a sensor associated with an existing ATP sensed subsequent movement activity. In an example monitoring system, operation 638 can detect an ATP changed based upon operation 624 operation 626 as explained above. In response to operation 638 determining that there is no ATP change, the monitoring system continues in the supervisory mode. In response to operation 638 determining that there is an ATP change, changed ATP information is sent to rules management operation 418, which records and updates the new information. Changed ATP information also is sent to the master AI system 424. A role of master AI operation 424 is to act as a gate keeper function and determine, if any of underlying AI function signals a change that is large enough to require other AI functions to recalibrate and require a retraining of other ML processes. For example—if a change in an ATP is determined, then the master AI operation 424 determines whether the ML models that determine TAP, for example, should be recalibrated based on the ATP change, which would then mandate a refresh of the training data set and one or more machine learning processes. More particularly, for example, as sensor data accumulates over time from daily activity generated by a resident an example master AI system 424 uses techniques of General Adversarial Networks (GAN) and applying linear regression models periodically to establish common use patterns and movements inside a dwelling. The master AI system operation 424 feeds back the common use/baseline/normal pattern information to the AI ATP builder operation 608 for use in building ATPs, which changed ATP information also is sent to machine (ML) system 1900, which performs the individual AI operations describe in this disclosure operations. An example ML system 1900 uses techniques including Naïve-Bayesian and Random Forests to generate training models, and further for automatic calibration. The calibration process further exposes and diagnoses changes in behaviors or abilities. Such diagnoses may be further forwarded to the responsible party, a member of a care circle, for clinical evaluation by medical professional or third-party Applications and third-party users, for example.

Operation 640 recommends/generates new ATP data. More specifically, in an example monitoring system 1200, operation 608 inputs one or more ATPs at setup. Operation 640 calibrates ATPs based on new ATP data that is generated as resident moves through the dwelling. For example, on a condition that a movement activity is sensed in a different part of the dwelling that did not previously have an ATP, such as an area of the house not previously traversed, then this new activity is recorded, and operation 640 creates a new ATP, which is added to an existing set of ATPs. Moreover, on a condition that a change in ATP is detected, then operation 640 records an NIP adjustment to cause a change of the ATP. Thus, ATPs can evolve over time based upon behavior of the resident.

Figure 9:
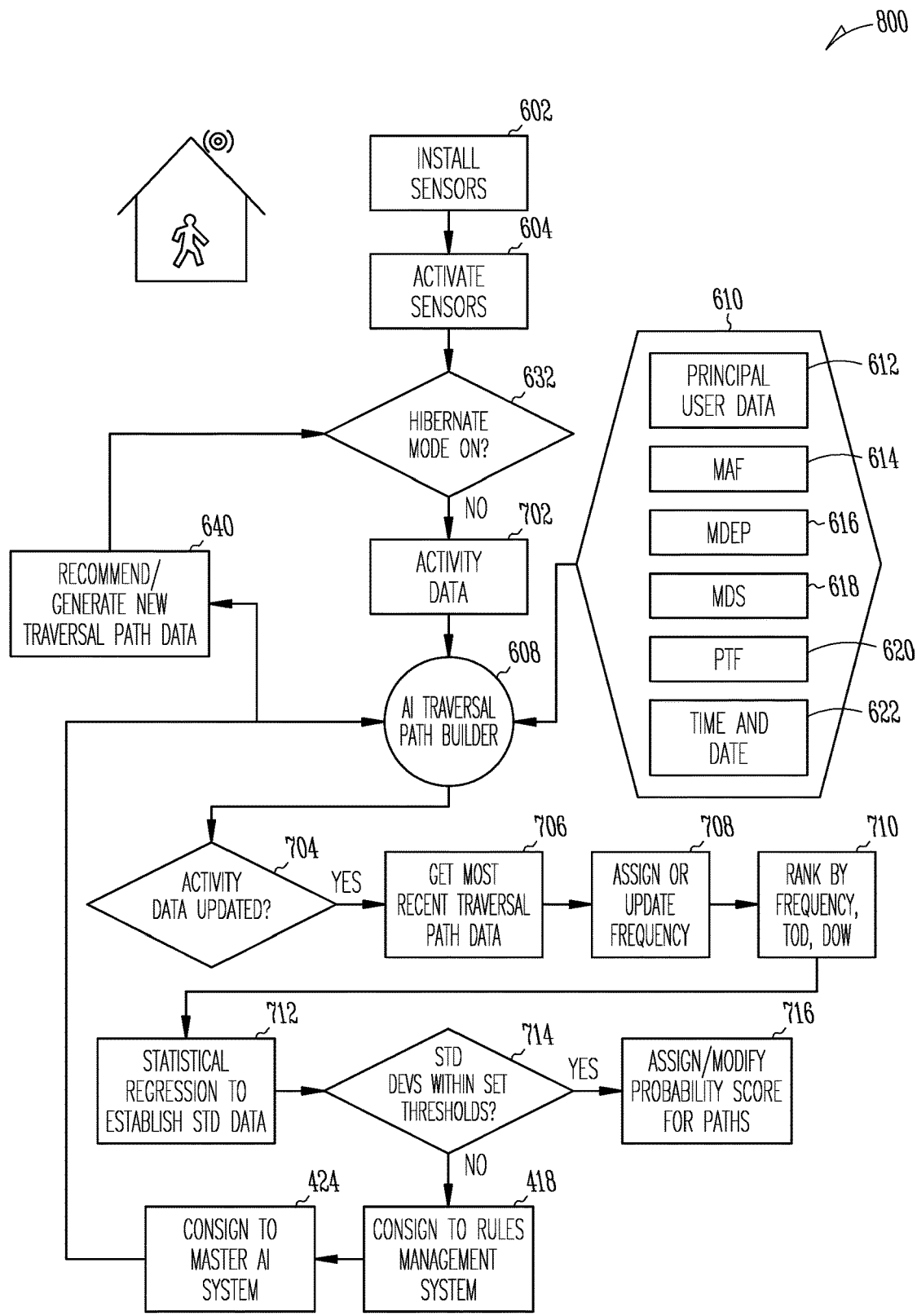
FIG. 9 is an illustrative flow diagram of an example process to determine path traversal frequencies (PTFs) and to update ATPs based upon PTFs.

FIG. 9 is an illustrative flow diagram of an example process 800 to determine path traversal frequencies (PTFs) and to update ATPs based upon PTFs. The PTFs and adjusted ATPs, in turn, are used to train the model 540. One or more computing machines 2100 are configured using executable instructions stored in a non-transitory memory device that when executed, cause processor circuitry to perform one or more of the operations of the process 700. The process 800 of FIG. 8 shows additional example details of an example decision operation 581 of FIG. 5C. PTFs are representative of frequently used paths or popular paths that are commonly used such as paths from bedroom to bathroom or living room to kitchen. However, these paths may change and hence the ranks have to be updated in line with the changes. An ATP is like a blueprint of for a path, and a PTF is an attribute of an ATP that indicates how frequently the path is traversed. Moreover, As explained below, PTFs also are used to adjust ATP rankings. PTF information is used to determine and rank frequently used ATPS. For example, assume that a resident walks from living room to bedroom three times a day, bedroom to bathroom six times a day and so on. Initially the PTF values are set from manual process 428, shown in FIGS. 6A-6B. A supervisory observation period is set. The observation period varies by resident and is dependent on the person's lifestyle, activity levels, abilities, and comorbid conditions. The example process 700 uses the install sensor operation 602 and the activate sensor operation 604. For economy of disclosure, operations explained earlier in this application will not be explained again. Operation 632 checks whether hibernate mode is active. In response to the hibernate mode off, the AI ATP builder operation 608 receives activity data 702, which can include a sensor data stream collected using the installed sensors. The AI ATP builder operation 608 causes operation 704 to determine whether activity data is updated. Updating of activity data can result from one or more sensors sensing movement of a resident within the dwelling. The AI ATP builder 608 uses algorithmic observation using neural ranking models and machine learning techniques to establish Path Traversal Frequency (PTF) for ATPs.

Still referring to FIG. 9, machine learning using neural ranking models are used at operation 710 to establish new path ranks based upon PTFs, which then becomes the basis for establishing dynamic PTFs. Moreover, Not only is an PTF an attribute of an ATP but also is a dynamic input to a regression model used to determine a change in an ATP pattern. For example, assume that person goes from bedroom to bathroom six times a day. But let's say the person has a UTI, then the frequency of bathroom visits for the next five days will increase to twenty. This is not normal. So, an alert is sent out as explained above to indicate a change in behavior. Meanwhile, a regression model will use historical data to determine if there is a deviation from the standard behavior. When the bedroom to bathroom traversal frequency increases, the system has to decide whether or not this is a permanent change. So, in the short term, the system tends to be a "wait and watch" mode—and does not "recalibrate"—But if this is a permanent change—then the PTF is set to twenty and hence an ATP algorithm adjusts a ranking of the bedroom to bathroom ATP.

The machine learning techniques described above with reference to FIG. 8 can be used with time of day (TOD) and day of week (DOW) values, collectively represented as time and date data to establish baseline PTF values for the time of day and day of week for ATP. For example, assume that bedroom to kitchen path is traversed most between 6:00 am and 8:00 am but is rarely traversed between 8:00 am and 10 am on Saturdays. Once the basic path ranks are set, the monitoring system assigns probability scores to the paths based on activity and behavior inside the home, once again, ensuring the most updated data are being used to monitor and report on ambulatory disruptions, Once assigned, this information is used to retrieve the most likely paths to be traversed during different time intervals to set traversal paths. This information is used to infer deviation from the norm e.g., failed to traverse a path from Bedroom to Bathroom in the morning. Additionally, the path ranking algorithms can be set to a Hibernation mode when there is a prolonged presence of a family member or caregiver or extended absence of the senior member in the dwelling unit. This can be necessary to adjust and prevent the automatic recalibration of PTFs and ATPs while a resident is absent from the dwelling. If a resident is going through a hospitalization period or post-operative convalescence period, a caregiver or family member might be present in the home for prolonged periods of time. In such case, in order to prevent activity data contamination, the monitoring system may be transitioned to a hibernation mode and the process that automates the ranking recalibration is temporarily paused. Hibernation mode can also be set, when a resident chooses to go on vacation or holidays.

More particularly, still referring to FIG. 9, in response to a determination that there is updated activity data, the AI ATP builder 608 causes operation 706 to get the most recent updated activity data. Updated activity data can include information identifying one or more ATP events. Each ATP event can include identification of an ATP path and a time and day at which the person was sensed during the event, at each sensor associated with the ATP. Operation 708 updates frequency of occurrence information for ATPs within the dwelling based upon the most recent ATP traversal data. Operation 710 ranks ATPs with a risk score indicating frequency of traversal at different times of day and days of week. The example risk scoring chart of FIG. 4 shows example risk scores. Operation 712 computes a statistical regression to establish standard deviation limits or buffer of acceptable range for frequency, TOD and DOW for the ATPs. For simplicity assume the inhabitant typically walks from bedroom to living room in the morning between 8:00 and 8:15 AM every day. A change in his condition could make him change this behavior and the resident now traverses this path at between 10:00 am and 10:15 AM. If the Standard deviation is set as one hour, then a two hour difference, could result in an alert situation. However, if this behavior persists over a period of time, then a default time for the said ATP is updated to reflect the new time. Operation 714 determines whether the standard deviations are within set thresholds, which. In response to a determination that the standard deviation for a frequency of occurrence of an ATP is within a set threshold, operation 716 assigns or modifies a probability of occurrence indicated as a risk score in FIG. 4, for a corresponding ATP based upon the activity data for that ATP, The example master AI system 424 uses ML techniques described above to learn changes, calibrate ATP adjustments and changes defaults. Operation 640 recommends/generates new ATP data as explained above with reference to FIG. 8. It is noted that with when the system is in hibernate mode, when there is change in data because of change in activity, there is a provision in the system to alert the AI not to calibrate/relearn because the system is in hibernate mode.

FIG. 10 is an example user interface display used for initiation and de-initiation of the hibernation process. Hibernation is an indication of the state of the home and the resident. The hibernation process is turned on when a resident is not generating sensor data—data that is necessary for the alerting, dashboard and AI to function. During the hibernation mode, the system will continue to monitor for sensor activity—however, feedback based on the daily activity is not transmitted to the master AI System. This ensures that machine learning models are trained based on known and determined sensor data streams and not based on the absence of the data.

Figure 11:
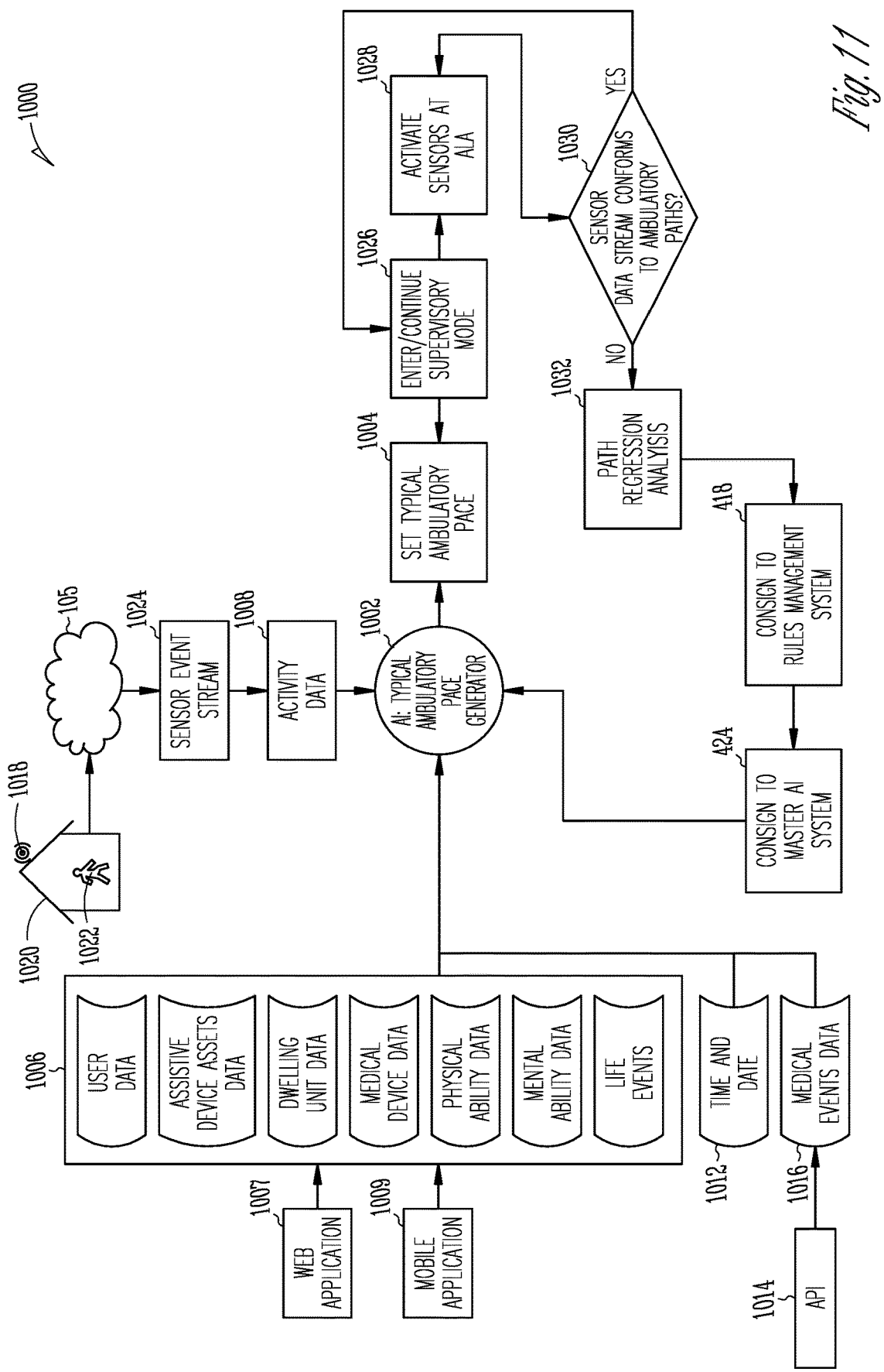
FIG. 11 is an illustrative flow diagram of an example process to determine a typical ambulatory pace (TAP) of a resident.

FIG. 11 is an illustrative flow diagram of an example process 1000 to determine a typical ambulatory pace of a resident. A computing machine 2100 is configured using executable instructions stored in a memory device that when executed, cause processor circuitry to perform one or more of the operations of the process 1000, As used herein, the term "typical ambulatory pace" (TAP) refers to the pace at which a resident moves within a dwelling. A TAP can be used to predict a time interval between a time when a resident's movement is detected by a sensor at one terminal point of an ATP and a predicted time at which the resident is expected to be detected by a sensor at a different terminal point of the ATP. Failure of the resident to traverse an ATP within an expected time interval can be cause for alarm.

More particularly, in an example monitoring system 1200, every event generated by the sensor has a timestamp that is recorded at the time of sensor activation. Sensor activation occurs from a movement, touch, presence, visual or vocal action by a senior. The Sensors are activated as the resident moves in and about in a dwelling. By chaining a series of these sensor activations and their timestamps and using runtime data. The monitoring system generates TAP for the resident. An example TAP can be measured in feet/sec. Computed value is deemed unique to the resident and is expected to change frequently. Physiological, activity levels and life events will impact the value of the ambulatory pace. Additionally, TAP can be adjusted using allowances based on when the resident is using assistive devices such as walker, or has had a hip replacement or knee surgery, for example.

Still referring to FIG. 11, the AI TAP generator 1002 causes operation 1004 to generate one or more TAPs for a resident based at least in part upon runtime data 1006, current activity data provided by operation 1008, and master AI system information provided by operation 424. A resident may have different TAPs for different ATPs. Runtime data 1006 can be provided over a network (not shown) via a web application or via a mobile application. Example runtime data received by the AI TAP generator 1002 includes information concerning characteristics of the resident and of the dwelling, Example runtime data includes user data (e.g., height, weight, loss of physical ability), assistive device assets data (e.g., wheelchair, walker), dwelling unit data (e.g., MAF, MDEP, MDS), medical device data, physical ability data, mental ability data, and life events data. The AI TAP generator 1002 also receives current time and date information 1012. An API 1014 can provide access over the network to medical events data 1016, which is provided to the AI TAP generator 1002.

One or more sensors 1018 (only one shown) at a dwelling 1020 can sense activity of a resident 1022. The one or more sensors 1020 are coupled to communicate information over the network 105 indicating ATP events within the dwelling 1020. Operation 1024 receives a stream of ATP events over the network 105. Operation 1008 provides activity data corresponding to the sensor events to the AI TAP generator 1002.

The AI TAP generator 1002 takes into account user data 1006 and sensor event stream 1024 to generate default ambulatory "walking" pace and to cause operation 1004 to generate one or more TAPs. Operation 1026 causes monitoring system to enter a supervisory mode supervisory mode that anticipates one or more ATPs that a resident may traverse based at least in part upon the activity data provided by operation 1008, Operation 1028 causes activation of sensors at terminal points of the anticipated ATPs to monitor for sensing movement of the resident. Operation 1030 determines whether the received activity data conforms to anticipated ATPs. If yes, then operation 1026 continues to cause the monitoring system to operate in the supervisory mode. If no, the operation 1032 performs a regression analysis to assess if there is a change in the traversal path or pace based on user data, Basically, the system checks if there was a detour or if the pace changed because of something else. If it is a one-time change, the system ignores and does not treat is as alert. However, if this change is permanent—which is determined by analysis a series of historical data. Operation 418 receives the input from the regression analysis which is then used to calibrate the ATP or TAP or both. The example master AI system 424 uses ML techniques described above to learn changes and to calibrate ATP and TAP adjustments.

Figure 12:
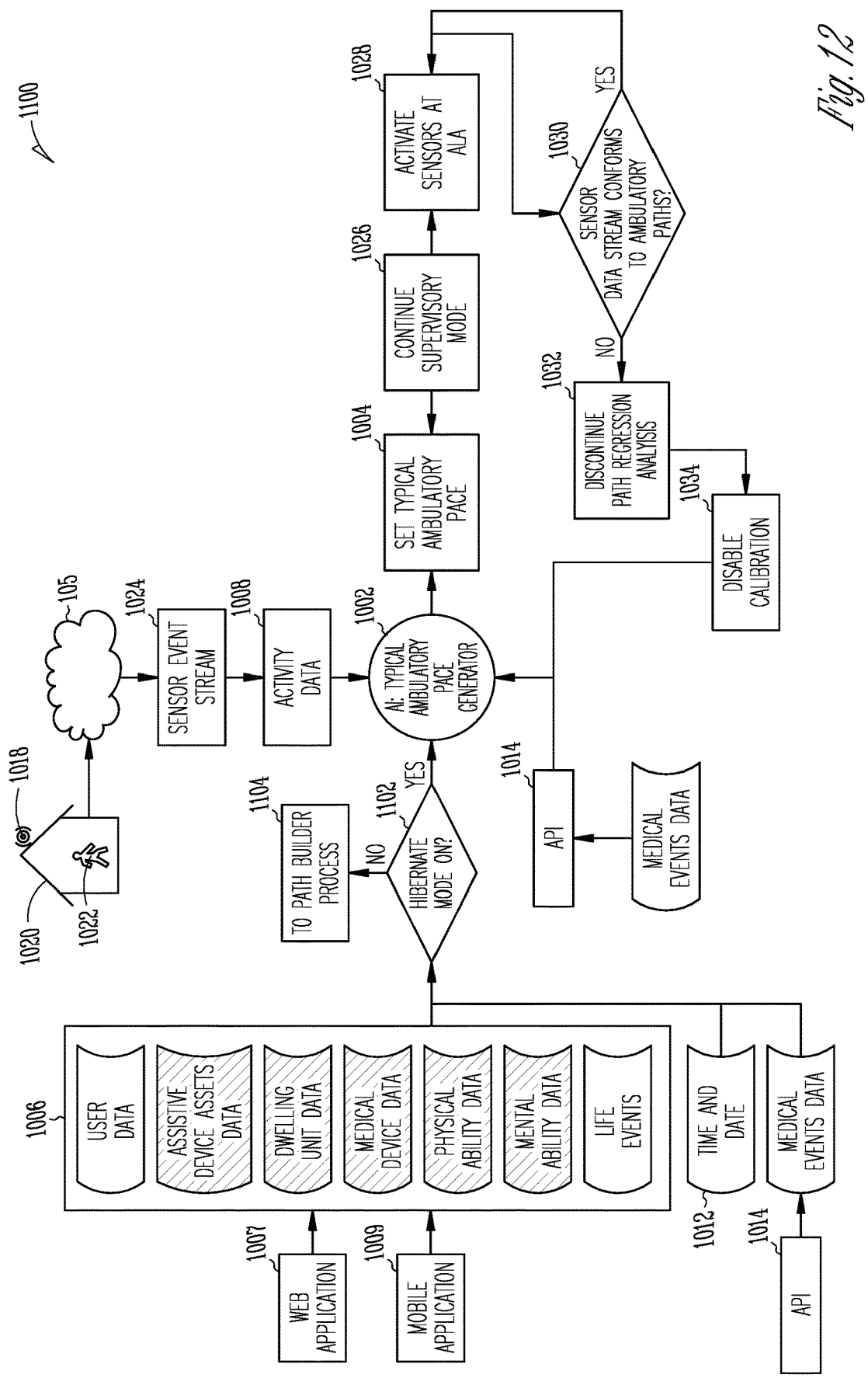
FIG. 12 is an illustrative flow diagram of an example operation of process of FIG. 11 during a hibernation mode.

FIG. 12 is an illustrative flow diagram of an example process 1100 to determine a typical ambulatory pace during a hibernation mode. One or more computing machines 2100 can be configured using executable instructions stored in a non-transitory memory device that when executed, cause processor circuitry to perform one or more of the operations of the process 1100. For economy of disclosure, operations in the process 1100 that already have been described will not be described again with reference to FIG. 12. Care giver input provided at web application 1007 or at mobile application 1009 can be provided to control activation/deactivation of hibernation operation 1102. In response to input to deactivate hibernation mode, operation 1104 causes the monitoring system to activate an ATP, PTF and TAP processes described above with reference to FIGS. 7, 8, 11 and 12. In response to input to activate hibernation mode, operation 1104 causes the AI TAP generator 1002 to enter a hibernate mode in which operation 1032 discontinues regression analysis and operation 1034 disables a calibration process of ATFs, PTFs, TAPs. During hibernation mode operation, API 1014 is coupled to receive medical events data and to provide the information to the AI TAP generator 1002. A typical medical event may be like a discharge from the hospital after a hospitalization event. In this case the medical event would indicate to the TAP generator that the resident may in an indisposed or convalescent mode and to make allowance for operation 1024, where the number of sensor events may be lower and operation 1008 where the movement inside a home may be decreased.

Figure 13A:
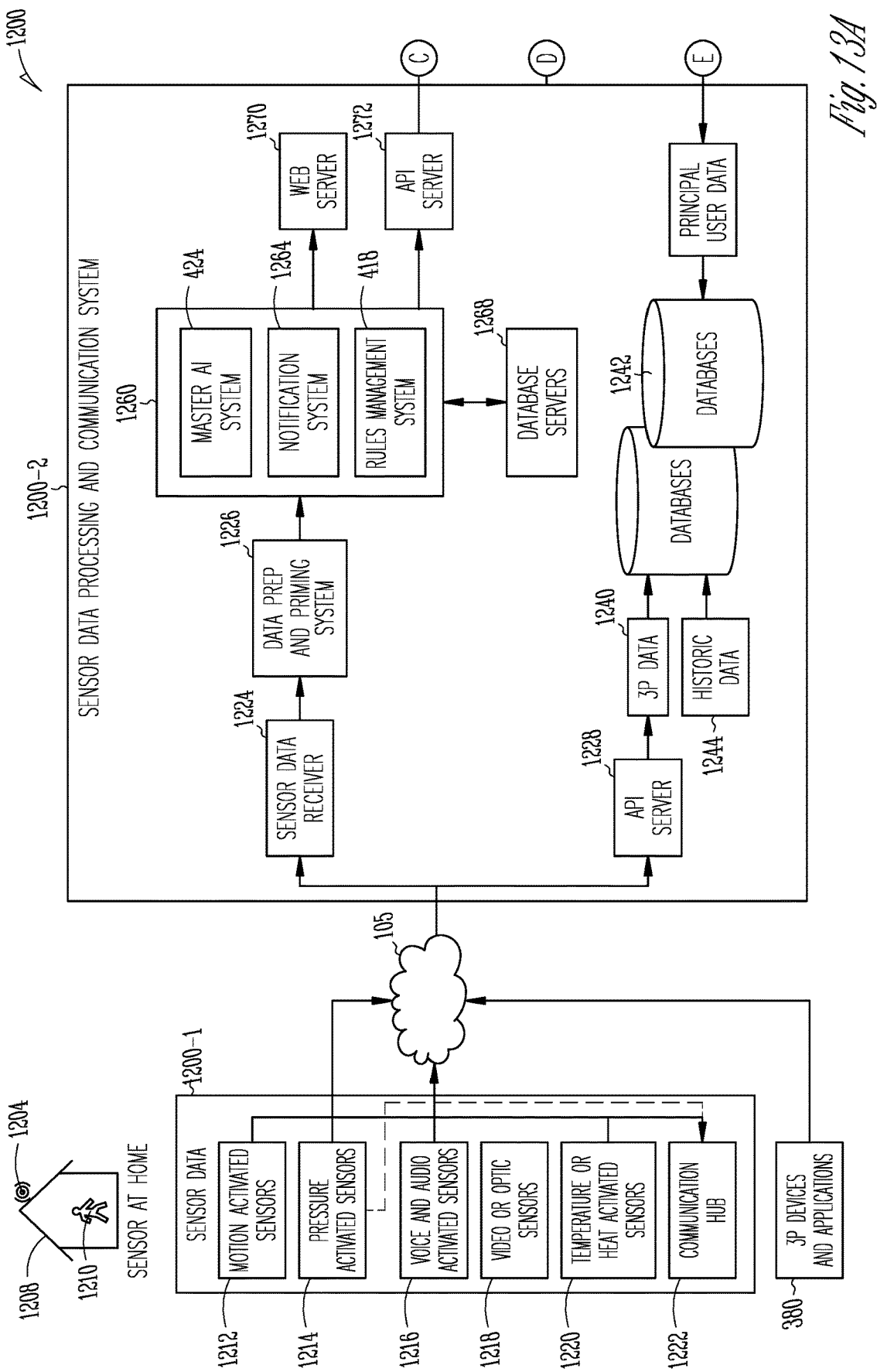
FIGS. 13A-13B are illustrative schematic diagrams representing an example monitoring system in accordance with some embodiments.
Figure 13B:
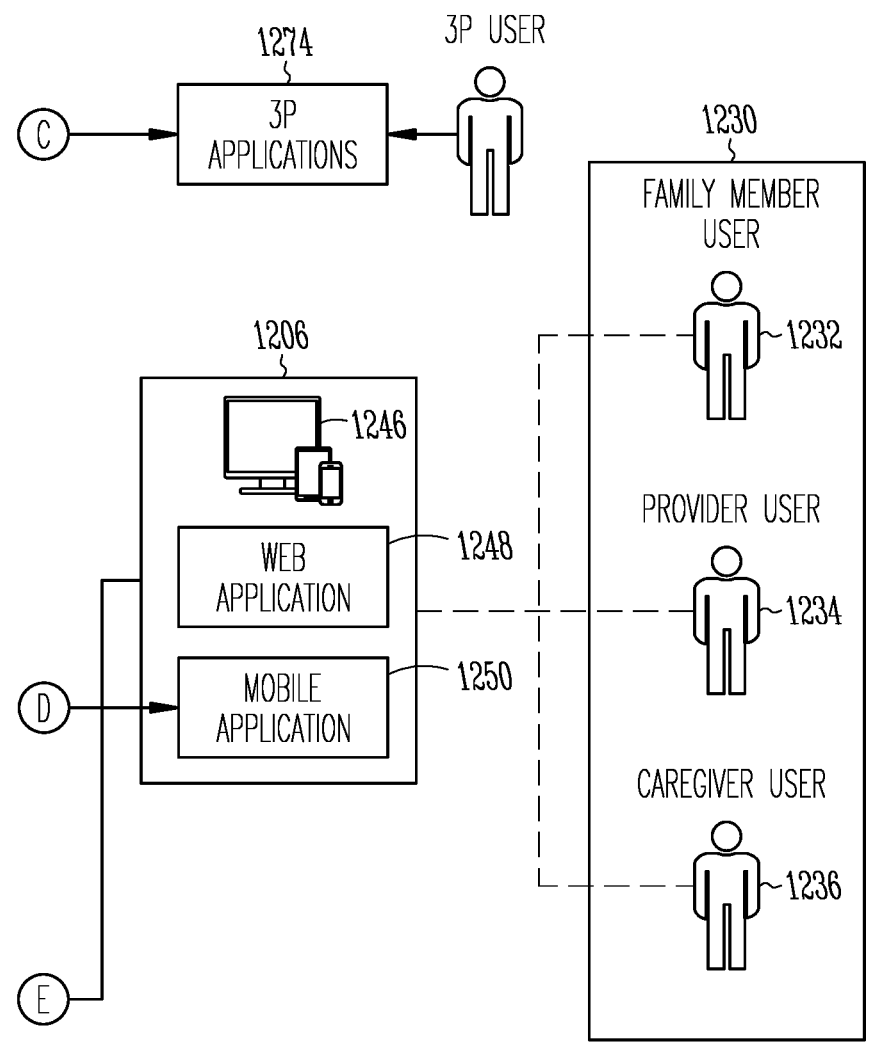

FIGS. 13A-13B are illustrative schematic diagrams representing an example monitoring system 1200 in accordance with some embodiments. The monitoring system 1200 includes a sensor data processing and communication system 1200-2, a sensor kit 1204, and a personnel communication system 1206 to communicate information with members of a care circle 1230, which can include family members 1232, caregiver providers (e.g., hospital) 1234, and caregivers (e.g., home healthcare workers) 1236. An example communication system 1206 can include client device 1246, that may include a desktop computer 1248 or a mobile device 1250. An example sensor kit 1204 can include multiple sensors installed at a dwelling 1208 to sense activity of a resident 1210. A sensor kit 1204 can include one or more types of sensors including motion activated sensors 1212, pressure activated sensors 1214, voice and audio activated sensors, 1216, video or optic sensors 1218, and temperature or heat activated sensors 1220. An electronic communication hub device 1222 is coupled to receive sensor data from the sensors 1212-1220 and to communicate the sensor data over a network 105 to the sensor data processing and communication system 1200-2.

The sensors of the monitoring system passively collect data. Once installed, the sensors work in the background and produce events as movement and other activity in a dwelling occurs. Not only does this type of system eliminate the need for monitored resident to continuously use, learn, interact with a device while requiring them to change their lifestyles, but it also de-synchronizes the resident 1210 from the monitoring group 1230. It enables the resident 1210 to go on about life through use of life-style integrated sensor kit, while keeping the care circle members 1230 informed and engaged via a notification system 1264 described below.

The sensor data processing and communication system 1200-2 includes a sensor data receiver 1224 to receive sensor data over the network 105. A preliminary processing circuit module 1226 is configured to perform data correction and modification to prepare the sensor data for further processing. An API server 1228 provides a programmatic interface to ingest user, dwelling, clinical and other data 1240 from third party (3P) applications and devices for storage in storage database system 1242. Historic data 1244 such as biometric data, activity data and physiological data also can be stored in a storage database system 1242. In addition, principal user data such as name, address, birth date, information about allergies, current medication or care plan, also can be entered from a data entry form presented via a graphical user interface (not shown) presented at a web client 1248 or at the mobile client 1250 for storing at the storage database system 1242.

An information management system 1260 includes a master AI Engine System 424, the notification system 1264, and a rules engine system 418. The information management system 1260 is coupled to receive sensor information from data preparation module 1226 and to receive data from the storage database system 1242 via database servers 1268. The information management system 1260 is coupled to provide output information to the care circle members 1230 via a web server 1270. The information management system 1260 is coupled to provide output information to third party applications 1274 via API server 1272.

The master AI system 424 encapsulates all of the underlying AI processes. The master AI operation 424 acts as a gate keeper, to capture feedback received from the different underlying child AI processes in the form of new data and to undertake a system reconciliation processes if needed. When feedback in the form of new data is received from one or more child AI processes, the master AI operation 424 performs an assessment and risk analysis of the impact of this feedback data. Depending on the risk assessment and factors, the operation 424 can signal one or more of the underlying child AI processes to initiate machine learning retraining. The operation 424 facilitates provisioning of the training data set to the child AI process. Where a process cannot be automated, the master AI operation 424 provides decision support data to assist human system administrators to initiate the process of retraining of child AI processes. Additionally, operation 424 maintains change logs of the modifications to training data sets, recalibration, and machine learning programs for posterity.

The notification system 1264 sends alert notifications. It is activated when the AI system identifies deviant patterns in the resident's condition. Alert notifications are sent to care circle members. Embedded in the notification system is a routing protocol that smartly routes alerts to designated care circle members e.g., medical alerts are routed to providers like doctors. However, alerts related to general activity and behavior can be sent both to the provider and a designated family member. Additionally, an escalation protocol has the ability to hierarchically escalate alerts to care circle members, if no action is taken on the alert.

The rules management system 418 captures and stores a set of rules or settings that are either manually configured or imported via API from different systems—for e.g., electronic medical records. These rules are important in setting the baseline behavior profile and pattern of the resident in the dwelling. Deviation from the rules forms the basis of how the AI System 424 determines deviant and anomalous behaviors and activates the Notification System 1264.

Figure 14:
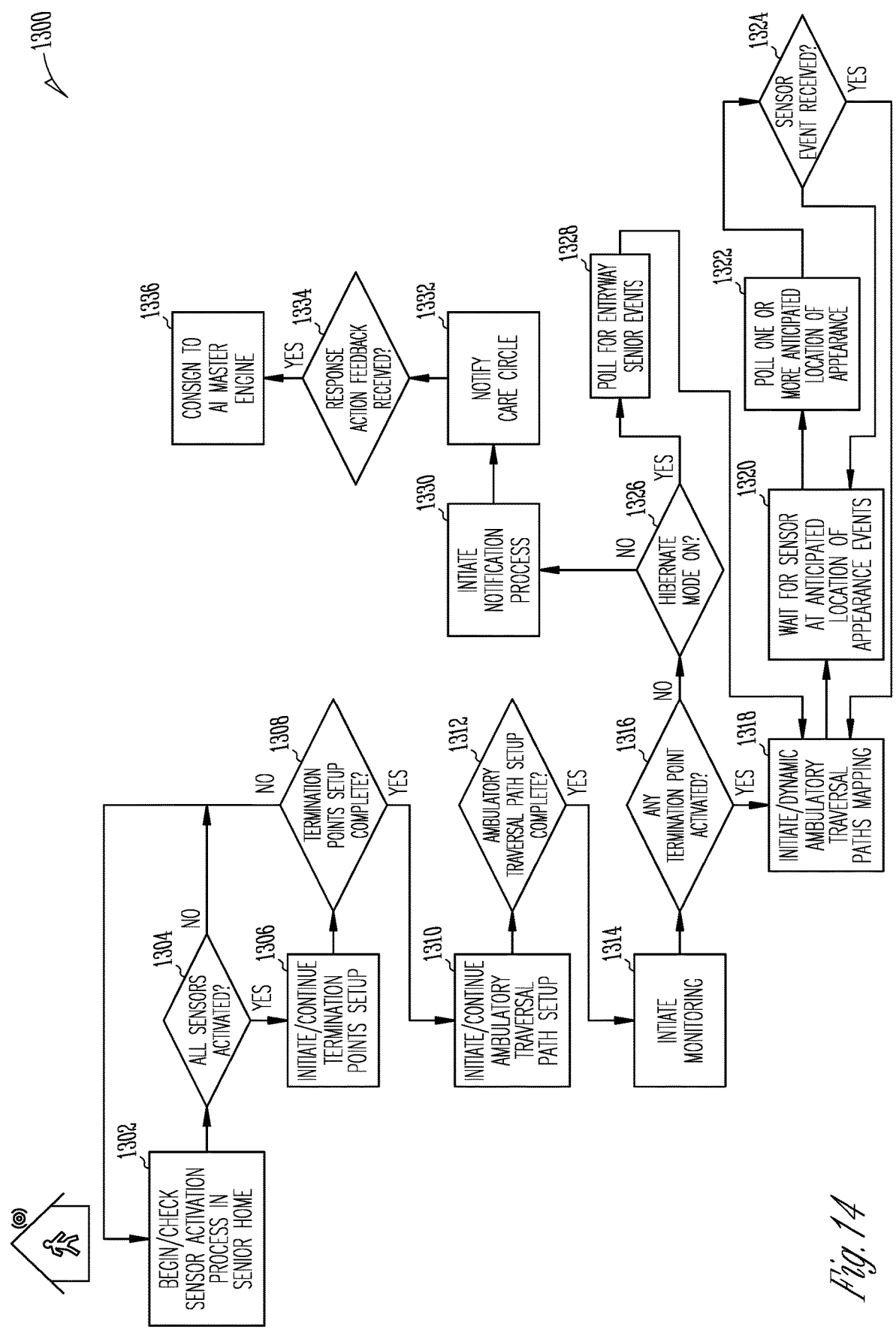
FIG. 14 is an illustrative flow diagram representing an example process for real-time monitoring of a resident.

FIG. 14 is an illustrative flow diagram representing an example process 1300 for real-time monitoring of a resident. One or more computing machines 2100 can be configured using executable instructions stored in a non-transitory memory device that when executed, cause processor circuity to perform one or more of the operations of the process 1300. Operation 1302 commences an activation process to activate sensors and setup ATPs. Operation 1304 determines whether all sensors are activated. In response to a determination that all sensors are activated, operation 1306 initiates/continues a termination point setup process, which involves configuration of these points in the system. Operation 1308 determines whether termination point setup is complete. In response to a determination that termination point setup is complete, operation 1310 initiates/continues ATP setup, which identifying the most like paths the resident is expected to take during a time period. Operation 1312 determines whether ATP setup is complete. In response to completion of ATP setup, operation 1314 enters a monitoring mode that listens for sensor activations. Operation 1316 determines whether any of the sensors sense activity.

In response to operation 1316 sensing a sensor event indicating activity by a resident, operation 1318 initiates TAP mapping, which involves establishing a baseline ambulatory pace as shown in FIG. 8. Operation 1320 waits for sensor at an anticipated locations where resident is expected to traverse to next, to sense movement activity, which involves identifying the traversal path as shown in FIG. 9. Operation 1322 polls sensors at locations where resident is expected to traverse to next. In operation, each sensor is polled to determine whether it has newly sensed data. If a sensor is triggered to sense information in response to an activity of a resident, then the sensor stores the sensed information in its associated sensor memory. The polling logic just reads from the sensors' memories to determine whether one or more sensors newly sensed data indicating that an occurrence of an activity event. Operation 1324 determines whether a sensor event at an anticipated location is received. In response to no receipt of an anticipated sensor event, control flows to operation 1320. In response to sensing an anticipated event, control flows back to operation 1318, which establishes the path. If the path matches an already established ATP—the system continues to process the next sensor event.

In response to operation 1316, not sensing a sensor event indicating activity by a resident, operation 1326 determines whether the monitoring system is in a hibernation mode. In response to determining that the system is not in a hibernation mode, operation 1328 polls sensors for entryway events generated by a door open close sensor. In response to determining that a sensor event involving resident movement in a hallway has occurred, control flows to operation 1318. In response to a determination that the system is in the hibernation mode, operation 1330 initiates a notification process. This condition is now indicative of an elopement scenario where no activity inside the house as determined through the absence of motion sensor data and a traversal path with an end point of an entryway. Operation 1332 sends notification to one or more members of the care circle 1230. A function of the notification is to generate and transmit an alert to a responsible party if and when a situation warrants intervention and action from a care circle member. Alerts are sent when there is an exception—in that, when a predicted behavior or outcome does not occur the system performs additional diagnosis, estimates the level of criticality, constructs the message structure to be delivered and distributes the message through the notification system 1264 to the responsible party. Operation 1334 determines whether feedback is received from a member of the care circle 1230, such as feedback indicating general condition of the patient, reports of any health conditions, a report of a fall incident or injury. Operation 1336 consigns to the AI master engine.

Figure 15B:
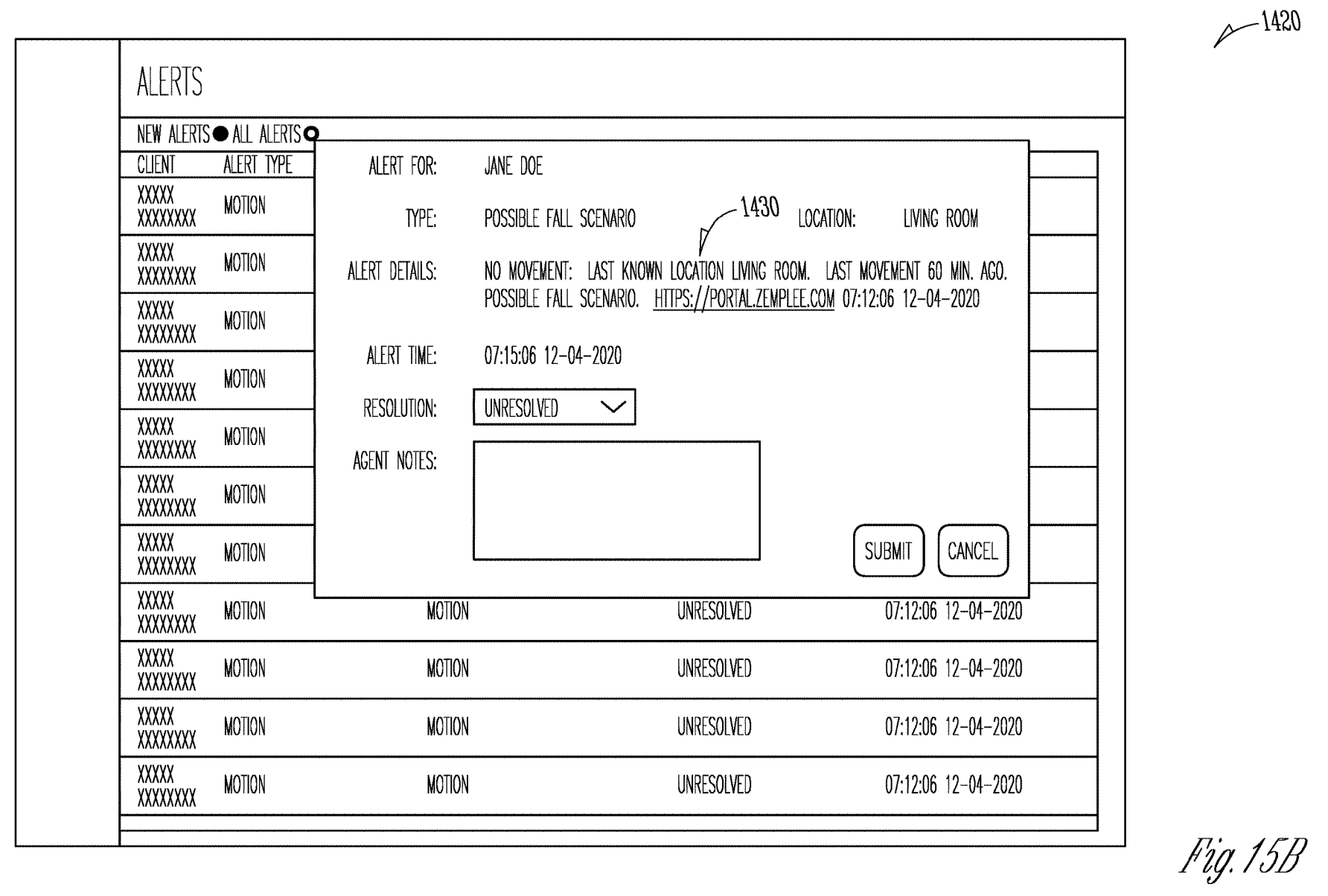
Figure 16B:
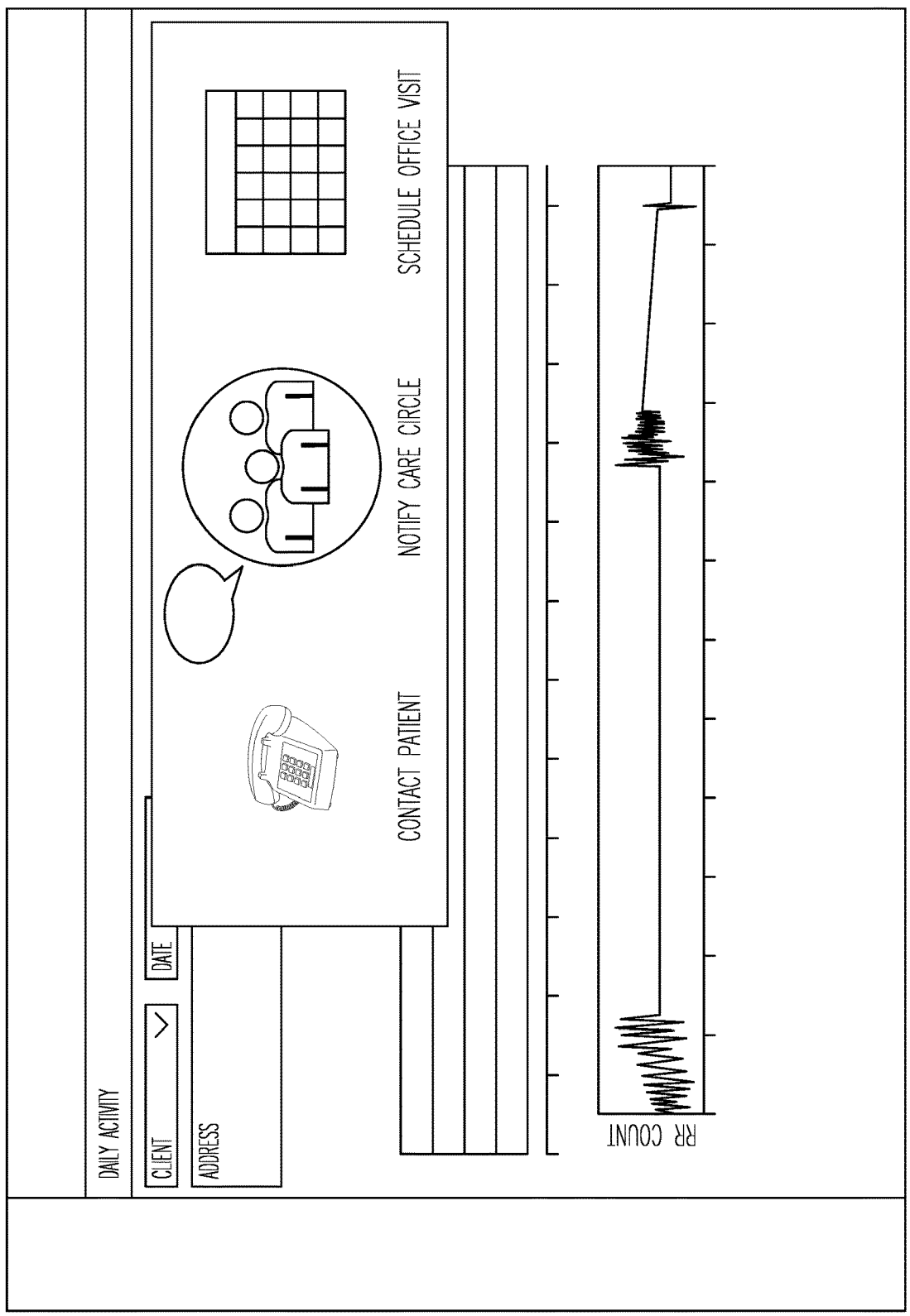
Figure 16C:
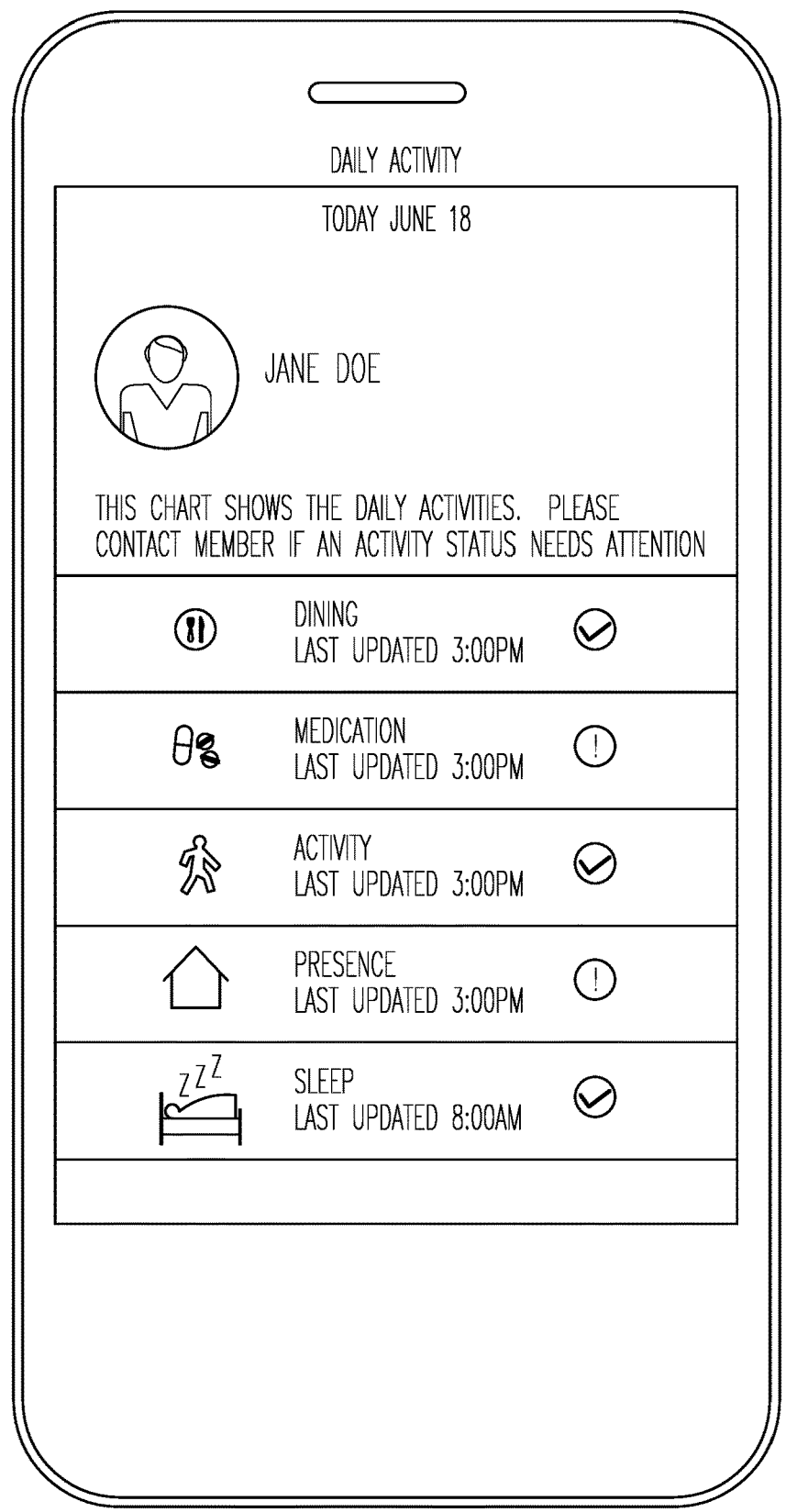
FIG. 16C is an illustrative drawing representing an alternative example patient activity update page.

FIG. 15A is an illustrative drawing representing an example alert message 1420 in care circle member's mobile phone or mobile application. FIG. 15B is an illustrative drawing representing an example alert message construct in an Alerts Dashboard 1420 of a web application 1248. FIG. 16A and FIG. 16B are illustrative drawings representing a Family and Caregiver Daily Activity Dashboard Page 1510 and Patient Activity Dashboard Page 1550 respectively in the web client 1248 or mobile application 1250. FIG. 16C is an illustrative drawing representing an alternative example patient activity update page. Alerts can be consumed on and actioned upon on client devices 1246. Different members of the care circle 1230 have the ability to take different actions in response to a notification. In an example monitoring system, every notification has a link to a real time view of a Daily Activity Dashboard Page 1510 or Patient Activity Dashboard Page 1550 for a resident. This page has additional features and functions, along with the required information for decision support and to facilitate further action. Upon receiving the message, a member of a care circle, is able, for example, to click on a hyperlink 1430 embedded in the message which directs the care circle member to the activity dashboard pages 1510 or 1550.

Figure 17:
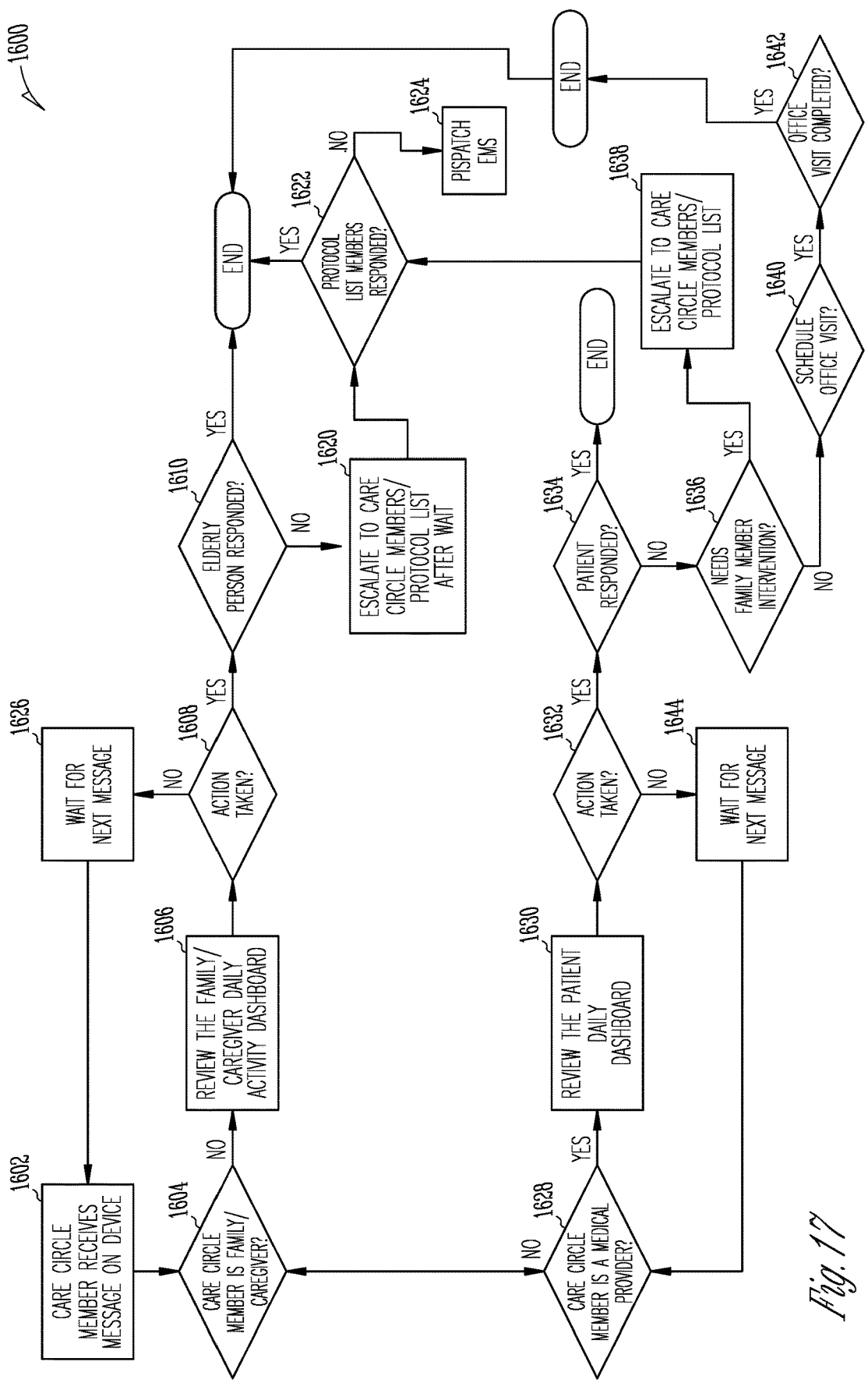
FIG. 17 is an illustrative flow diagram representing two illustrative example scenarios of an alert notification process.

FIG. 17 is an illustrative flow diagram representing two illustrative example scenarios of an alert notification process 1600. One or more computing machines 2100 can be configured using executable instructions stored in a non-transitory memory device that when executed, cause processor circuity to perform one or more of the operations of the process 1600. At operation 1602, a member of the care circle 1230 receives a message concerning a resident on a device 1246. Operation 1604 represents a device of a caregiver/family member care giver determining whether the device has received a message concerning a resident. In response to the caregiver/family member device receiving the message, operation 1606 displays a Caregiver Daily Activity Dashboard Page 1510 on the device. Operation 1608 determines whether the caregiver/family member caregiver has taken action such as calling the resident on a phone. In response to operation 1608 determining that the caregiver/family member has taken action, operation 1610 determines whether the resident has responded. In response to a determination that the resident has responded, the process ends. In response to the resident not responding, operation 1620 escalates with a call to an additional caregiver based upon a list of additional caregivers. Operation 1622 determines whether the escalated caregiver has responded. In response to a determination that no additional caregiver has responded, operation 1624 dispatches an Emergency Medical Service (EMS) team and the process ends. In response to a determination at operation 1622 that a family member/caregiver has responded, the process ends. Also, in response to operation 1608 determining that the caregiver/family member has not yet taken action, operation 1626 waits for a next message and returns control to operation 1602.

Operation 1628 represents a device of a medical provider member care giver determining whether the device has received a message concerning a resident. In response to the caregiver/family member device receiving the message, operation 1630 displays a Patient Daily Activity Dashboard 1550 on the device. Operation 1632 determines whether the medical provider caregiver has taken action such as calling the resident on a phone. In response to operation 1632 determining that the medical provider has taken action, operation 1634 determines whether the resident has responded. In response to a determination that the resident has responded, operation 1636 determines whether the resident requires family member intervention. In response to a determination at operation 1636 that the resident requires family member intervention, operation 1638 escalates with a call to a caregiver family member based upon a list of additional caregivers. Control flows to operation 1622, which determines whether the escalated caregiver has responded. In response to a determination that no additional caregiver has responded, operation 1624 dispatches an EMS team and the process ends. In response to a determination that the additional family member/caregiver has responded, the process ends. Also, in response to operation 1632 determining that the medical provider has not yet taken action, operation 1644 waits for a next message and returns control to operation 1628.

Figure 18:
FIG. 18 is an illustrative drawing representing an example Alert Resolution and Feedback page displayed on a user device in a web client or a mobile application.

FIG. 18 is an illustrative drawing representing an example Alert Resolution and Feedback page displayed on a user device 1246 in a web client 1248 or a mobile application 1250.

Figure 19:
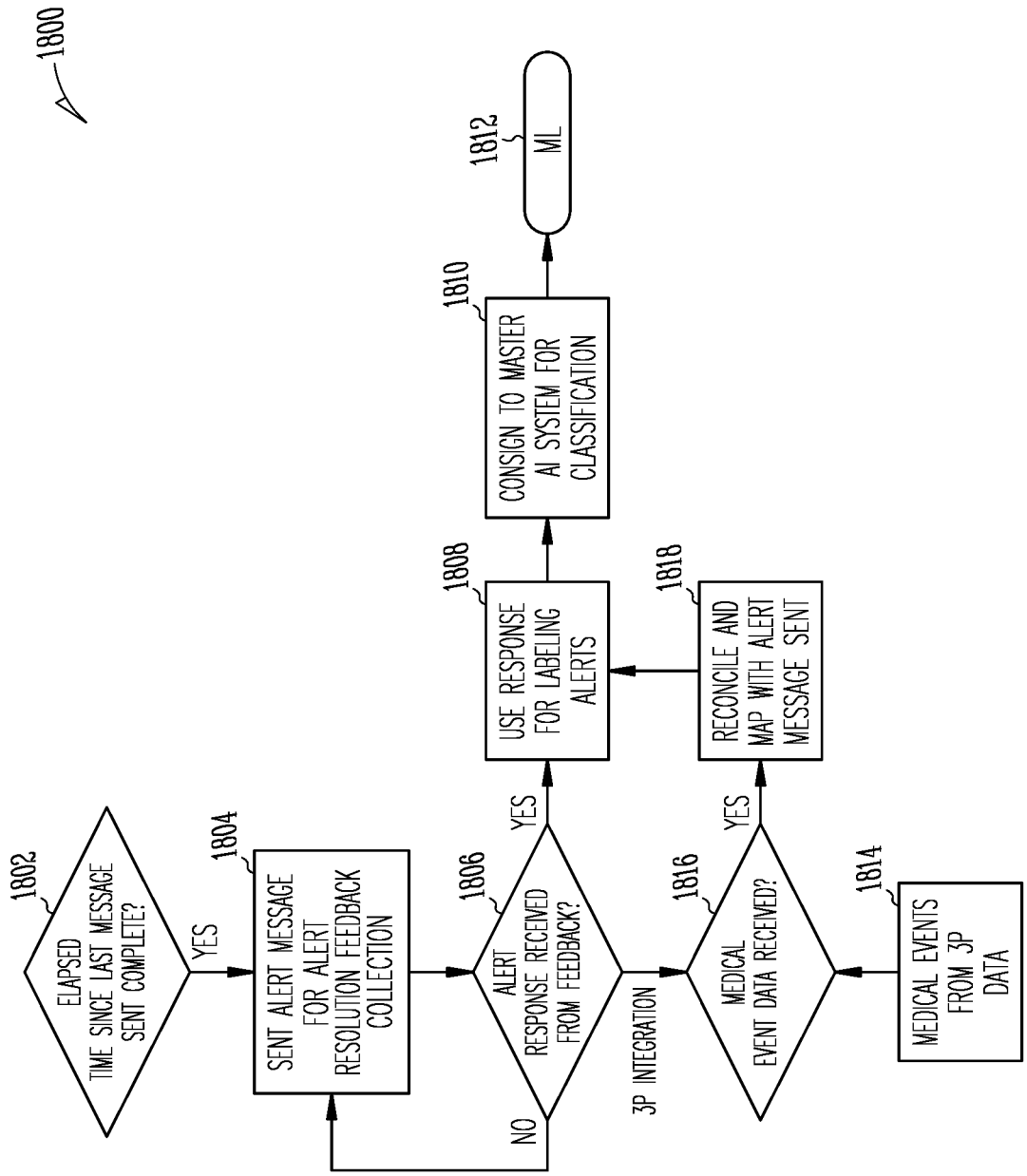
FIG. 19 is an illustrative flow diagram representing an example process to display an example Alert Resolution and Feedback page.

FIG. 19 is an illustrative flow diagram representing an example process 1800 to display an Alert Resolution and Feedback page. Capturing feedback response on the action taken to remediate a situation arising from a change in the behavior pattern which might indicate a life-threatening situation is an important function. The monitoring system uses machine learning and training algorithms use behavior pattern data and operate to refine and improve the quality of alerts and notifications. The process 1800 of FIG. 19 represents two approaches to capturing feedback data response.

A first approach shown in FIG. 19 involves survey response from the care circle member responsible for taking the remedial action for the elderly. This first approach uses a passive way of supervised learning to train the AI for labelling and classification of events. Operation 1802 determines whether a predetermined amount of time has elapsed time after an incident has occurred. In response to a determination that the predetermined amount of time has elapsed, Operation 1804 sends to a care circle member a message on a user device through one or more modalities. The message includes a link to the Alert Resolution and Feedback page which collects information about the type of response and the action taken to resolve the alert. Care circle members can choose one of the responses from the set of responses. Operation 1806 determines whether a response is received from a caregiver. Operations 1802, 1804 may make multiple iterative attempts to capture this information. Operation 1808 labels the alert based on the options forwarded to classification process. Operation 1810 sends the classified data to the master AI system 424 for machine learning 1812 from which new training models are built. This first approach involving passive labeling builds a history of data that is further used in regression models to further refine the quality of alerts and notifications. For example, based on the historic data the system will be able to identify fall incidents occurring during certain type of transitional activity, such as a bathroom visit or exit from bed.

A second approach shown in FIG. 19 involves 3P Data received from an API. For example, at operation 1814, through ADT (Admissions, Discharge and Transfer) data from 3P Hospital Information Systems and Clinical Information Systems, which many include key Medical and Life Events related to a consequent visit to a hospital, an outpatient clinical encounter or visit to the primary physician is collected. Operation 1816 determines whether medical event data is received. Operation 1818 reconciles the received medical data with the alert message sent previously to a Care Circle Member. Operation 1808 labels an alert determined to correspond to the medical data. Moreover, response data collected through 3P API integrations can be further used to calculate several business metrics that help business users establish value for the system, while realizing business benefits—for example, deducing unnecessary hospitalizations or converting them into outpatient encounters.

Figure 20:
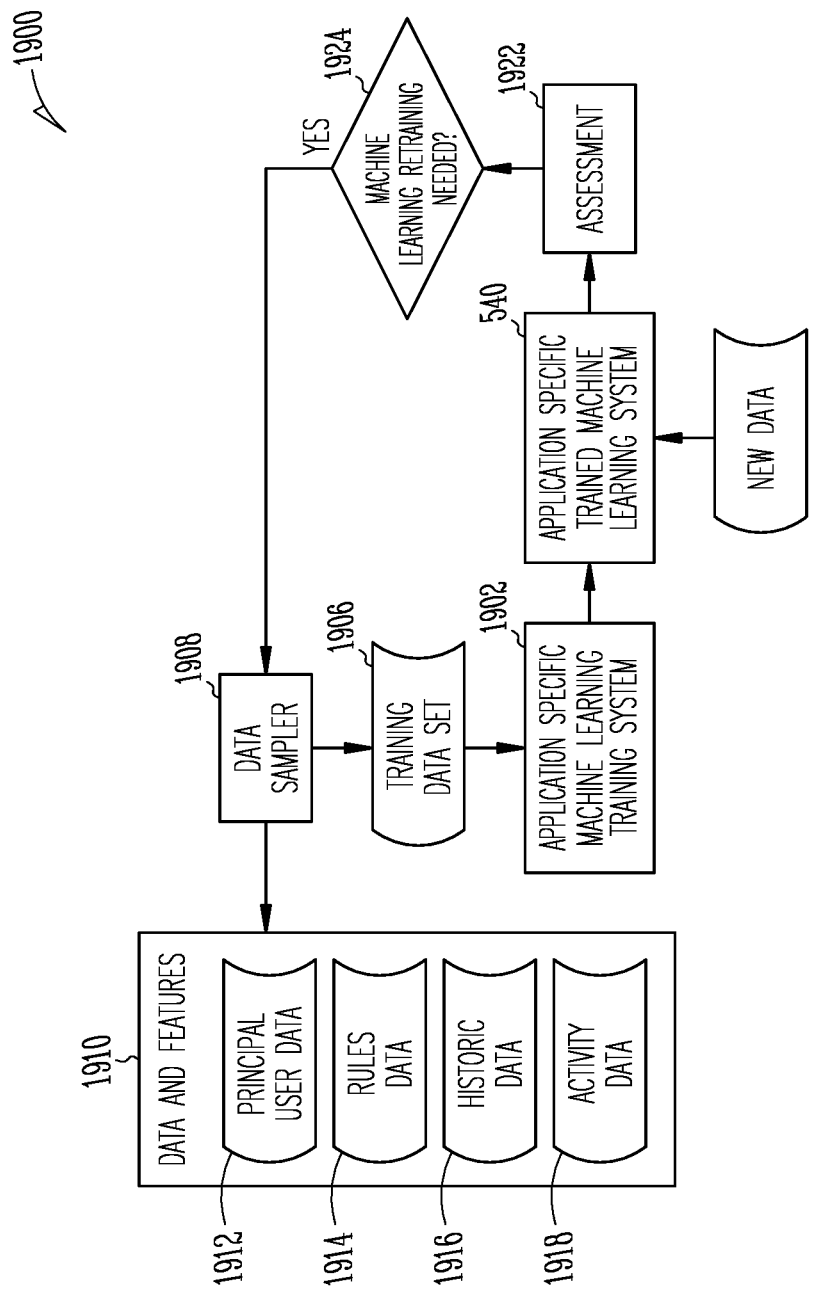
FIG. 20 is an illustrative drawing representing an example machine learning system used to produce machine learning trained models for evaluation of a resident's health in accordance with some embodiments.

FIG. 20 is an illustrative drawing representing an example machine learning system 1900 used to produce machine learning trained models for evaluation of a resident's health. One or more computing machines 2100 are configured using executable instructions stored in a non-transitory memory device that when executed, cause processor circuitry to perform one or more of the operations of the machine learning system 1900. Machine learning involves providing computers the ability to learn and apply or modify rules for computation without requiring explicit episodic programming. In essence, machine learning involved studying existing data, learning from existing data and making predictions about new data. A machine learning training operation 1902 produces a trained model 540 based upon a training data set 1906. A data sampler operation 1908 receives training data 1910, which includes principal user data (e.g., user height, weight, date of birth, user equipment such as wheelchair, dwelling data) 1912, rules data (e.g., go to bed, wake up schedule, dining, and medication schedule) 1914, historic data past activity data long term) 1916, and sensor data (e.g., present activity data) 1918—to produce one or more templates—for example daily living pattern of a resident). These templates are used to process runtime data 1920 such as sensor measurements taken at a dwelling. Assessment operation 1922 assesses, if the output from the new data calls for a change in the templates or the rules, Operation 1924 determines whether additional training is required based upon the runtime data. On a condition that additional training is required, operation 1924 causes data sampler operation 1908 to obtain additional training data to continue with model training. The example machine learning system 1900 is used to implement different instances of the master AI system operation 424 described in detail with reference to FIGS. 6A-6B, 8, 9, 11, and 12. Different AI system operation instances 424 can use different training operations to produce different trained models. As explained above, the master AI system operation 424 can use Logistic Regression (LR), Naïve-Bayesian, Neural Networks, General Adversarial Networks (GAN), Random Forests and other tools. The main purpose of using these techniques is in classification and regression of data, pattern detection, ranking and probability scoring.

Computing Machine

Figure 21:
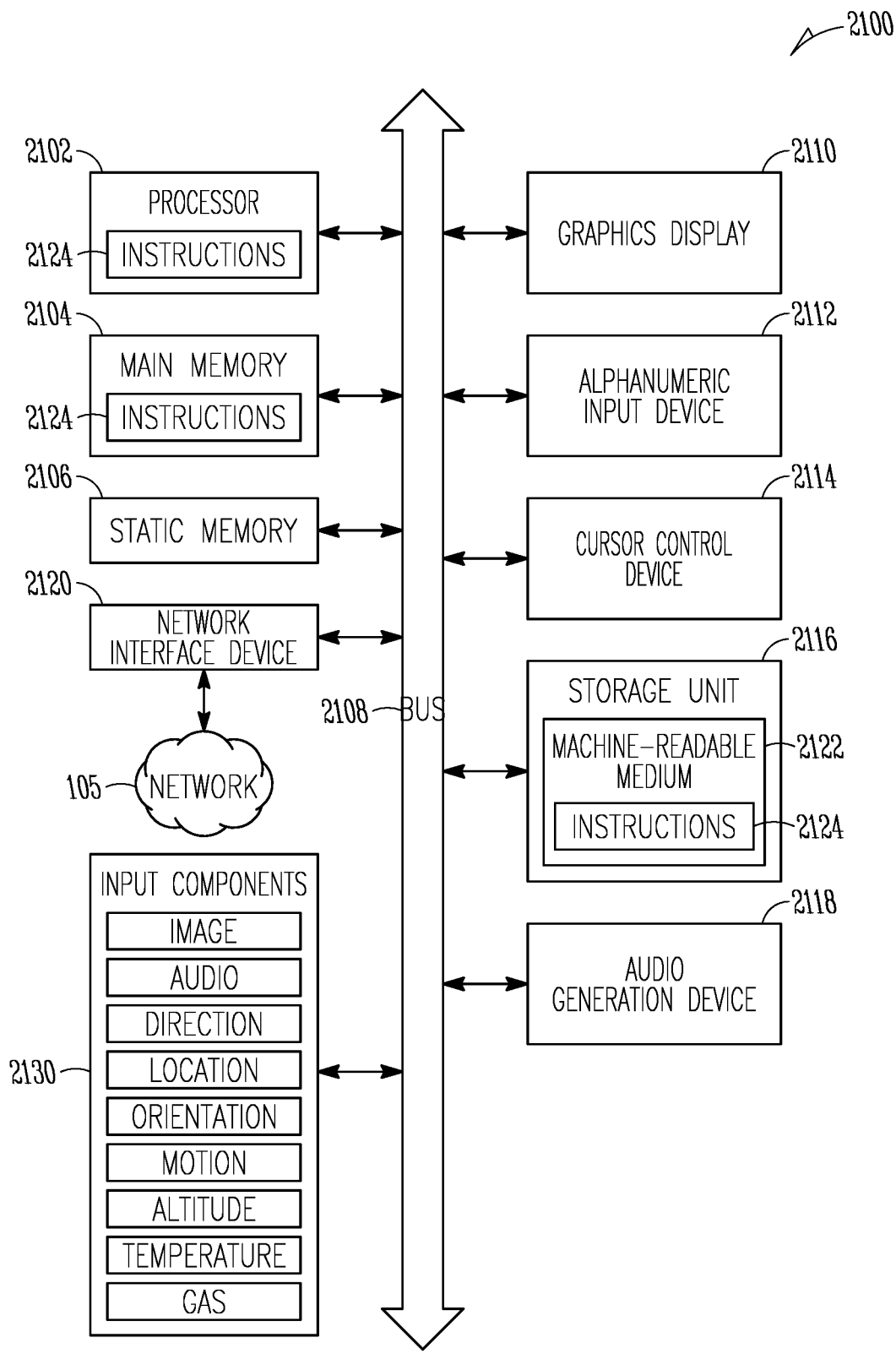
FIG. 21 is an illustrative drawing representing components of a n example computing machine, according to some embodiments.

FIG. 21 illustrates components of a computing machine 2100, according to some example embodiments, that is able to read instructions from a non-transitory machine-storage medium (e.g., a machine-readable storage device, a non-transitory machine-readable storage medium, a computer-readable storage medium, or any suitable combination thereon and perform any one or more of the methodologies discussed herein. Specifically, FIG. 21 shows a diagrammatic representation of the machine 2100 in the example form of a computing machine (e.g., a computer) and within which instructions 2124 (e.g., software, a program, an application, an applet, an app, or other executable code) for causing the computing machine 2100 to perform any one or more of the methodologies discussed herein may be executed, in whole or in part.

For example, the instructions 2124 stored in a non-transitory computer readable storage device may cause the computing machine 2100 to execute the flow diagrams of FIGS. 5A-5C, 6A-6B, 8, 9, 11, 12, 14, 17, and 20. In one embodiment, the instructions 2124 can transform the general, non-programmed machine 2100 into a particular machine (e.g., specially configured machine) programmed to carry out the described and illustrated functions in the manner described.

In alternative embodiments, the computing machine 2100 operates as a standalone device or may be connected (e.g., networked) to other machines. In a networked deployment, the machine 2100 may operate in the capacity of a server machine or a client machine in a server-client network environment, or as a peer machine in a peer-to-peer (or distributed) network environment. The computing machine 2100 may be a server computer, a client computer, a personal computer (PC), a tablet computer, a laptop computer, a netbook, a set-top box (STB), a personal digital assistant (PDA), a cellular telephone, a smartphone, a web appliance, a network router, a network switch, a network bridge, or any machine capable of executing the instructions 2124 (sequentially or otherwise) that specify actions to be taken by that machine. Further, while only a single machine is illustrated, the term "machine" shall also be taken to include a collection of machines that individually or jointly execute the instructions 2124 to perform any one or more of the methodologies discussed herein.

The computing machine 2100 includes a processor 2102 (e.g., a central processing unit (CPU), a graphics processing unit (GPU), a digital signal processor (DSP), an application specific integrated circuit (ASIC), a radio-frequency integrated circuit (RFIC), or any suitable combination thereof), a non-transitory main memory 2104, and a non-transitory static memory 2106, which are configured to communicate with each other via a bus 707. The processor 702 may contain microcircuits that are configurable, temporarily or permanently, by some or all of the instructions 724 such that the processor 2102 is configurable to perform any one or more of the methodologies described herein, in whole or in part. For example, a set of one or more microcircuits of the processor 2102 may be configurable to execute one or more modules (e.g., software modules) described herein.

The machine 2100 may further include a graphics display 2110 (e.g., a plasma display panel (PDP), a light emitting diode (LED) display, a liquid crystal display (LCD), a projector, or a cathode ray tube (CRT), or any other display capable of displaying graphics or video). The machine 2100 may also include an input device 2112 (e.g., a keyboard), a cursor control device 2121 (e.g., a mouse, a touchpad, a trackball, a joystick, a motion sensor, or other pointing instrument), a non-transitory memory storage unit 2116, a signal generation device 2118 (e.g., a sound card, an amplifier, a speaker, a headphone jack, or any suitable combination thereof), and a network interface device 2120.

The storage unit 2116 includes a machine-storage medium 2122 (e.g., a tangible machine-readable storage medium) on which is stored the instructions 2124 (e.g., software) embodying any one or more of the methodologies or functions described herein. The instructions 2124 may also reside, completely or at least partially, within the main memory 2104, within the processor 2102 (e.g., within the processor's cache memory), or both, before or during execution thereof by the machine 2100. Accordingly, the main memory 2104 and the processor 2102 may be considered as machine-readable media (e.g., tangible and non-transitory machine-readable media). The instructions 2124 may be transmitted or received over a network 2126 via the network interface device 2120.

In some example embodiments, the machine 2100 may be a portable computing device and have one or more additional input components (e.g., sensors or gauges). Examples of such input components include an image input component (e.g., one or more cameras), an audio input component (e.g., a microphone), a direction input component (e.g., a compass), a location input component (e.g., a global positioning system (GPS) receiver), an orientation component (e.g., a gyroscope), a motion detection component (e.g., one or more accelerometers), an altitude detection component (e.g., an altimeter), and a gas detection component (e.g., a gas sensor) Inputs harvested by any one or more of these input components may be accessible and available for use by any of the modules described herein.

Executable Instructions and Machine-Storage Medium

The various memories (i.e., 2104, 2106, and/or memory of the processors) 2102) and/or storage unit 2116 may store one or more sets of instructions and data structures (e.g., software) 2124 embodying or utilized by any one or more of the methodologies or functions described herein. These instructions, when executed by processor(s) 2102 cause various operations to implement the disclosed embodiments.

As used herein, the terms "machine-storage medium," "device-storage medium," "computer-storage medium" (referred to collectively as "machine-storage medium 2122") mean the same thing and may be used interchangeably in this disclosure. The terms refer to a single or multiple storage devices and/or media (e.g., a centralized or distributed database, and/or associated caches and servers) that store executable instructions and/or data, as well as cloud-based storage systems or storage networks that include multiple storage apparatus or devices.

The terms shall accordingly be taken to include, but not be limited to, solid-state memories, and optical and magnetic media, including memory internal or external to processors. Specific examples of machine-storage media, computer-storage media, and/or device-storage media 2122 include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms machine-storage media, computer-storage media, and device-storage media 2122 specifically exclude carrier waves, modulated data signals, and other such media, at least some of which are covered under the term "signal medium" discussed below. In this context, the machine-storage medium is non-transitory.

Signal Medium

The term "signal medium" or "transmission medium" shall be taken to include any form of modulated data signal, carrier wave, and so forth. The term "modulated data signal" means a signal that has one or more of its characteristics set or changed in such a matter as to encode information in the signal.

Computer Readable Medium

The terms "machine-readable medium," "computer-readable medium" and "device-readable medium" mean the same thing and may be used interchangeably in this disclosure. The terms are defined to include both machine-storage media and signal media. Thus, the terms include both storage devices/media and carrier waves/modulated data signals.

The instructions 2124 may further be transmitted or received over a communications network 2126 using a transmission medium via the network interface device 2120 and utilizing any one of a number of well-known transfer protocols (e.g., HTTP), Examples of communication networks 2126 include a local area network (LAN), a wide area network (WAN), the Internet, mobile telephone networks, plain old telephone service (POTS) networks, and wireless data networks (e.g., WiFi, LTE, and WiMAX networks). The term "transmission medium" shall be taken to include any intangible medium that is capable of storing, encoding, or carrying instructions 2124 for execution by the machine 2100, and includes digital or analog communications signals or other intangible medium to facilitate communication of such software.

In some embodiments, the network interface device 2120 comprises a data interface device that is coupled to one or more of an external camera 2130, an external microphone 2132, and an external speaker 2134 (e.g., external to the machine 2100). The camera 2130 may include a sensor (not shown) configured for facial detection and gesture detection. Any of the camera 2130, microphone 2132, and speaker 2134 may be used to conduct the presentation as discussed herein.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-storage medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured by software to become a special-purpose processor, the general-purpose processor may be configured as respectively different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application program interface (API)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification may be presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The invention claimed is:

1. A system to monitor a resident of a dwelling comprising:
   a plurality of sensors located at the dwelling to sense for resident activity at different locations at the dwelling and coupled to save at one or more non-transitory memories, sensor information providing indications of occurrences resident activity;
   one or more computing machines;
   non-transitory memory including instructions incorporated into the non-transitory memory, the instructions configuring the computing machine to perform operations comprising:
   identifying a location at the dwelling, of resident activity, based at least in part upon sensor information produced using a sensor located at the dwelling to sense resident activity at the identified location;
   using a machine learning trained model, trained based at least in part upon resident traversal activity between sensors at different locations of the dwelling to learn a plurality of anticipated traversal paths (ATPs) located at the dwelling each ATP having a first terminal point and a second terminal point, to identify one or more ATPs based at least in part upon the identified location, the one or more identified ATPs each having a first terminal points associated with the identified location and having a second terminal point associated with a different location at the dwelling;
   determining whether the sensor information indicates an occurrence of resident activity at a location at the dwelling corresponding to a second terminal point of at least one of the one or more identified ATPs; and
   causing sending of an alert indicating a failed ATP traversal event, on a condition that the sensor data indicates for each of the one or more identified ATPs, no occurrence of resident activity at a location of the dwelling corresponding to the second terminal point of the identified ATP.

2. The system of claim 1,
   wherein the plurality of sensors includes a plurality of motion sensors.

3. The system of claim 1 the operations further including:
   receiving information indicating successful resolution of the failed ATP traversal event;
   determining based in part upon the communication indicating successful resolution of the failed ATP traversal event whether the resident's traversal activity pattern has changed;

based on a determination that the resident's traversal activity pattern has changed, retraining the machine learning trained model.

4. The system of claim 1,
wherein the plurality of sensors are coupled to save at one or more non-transitory memories, sensor information providing indications of occurrences and times of occurrences of resident activity;
wherein identifying includes identifying a location at the dwelling, of resident activity at a first time, based at least in part upon sensor information produced using a sensor located at the dwelling to sense resident activity at the identified location;
wherein determining includes determining whether the sensor information indicates an occurrence within a predetermined time interval after the first time, of resident activity at a location at the dwelling corresponding to a second terminal point of at least one of the one or more identified ATPs; and
wherein causing sending of an alert includes causing sending of an alert indicating a failed ATP traversal event, on a condition that the sensor data indicates for each of the one or more identified ATPs, no occurrence within the predetermined time interval after the first time, of resident activity at a location of the dwelling corresponding to the second terminal point of the identified ATP.

5. A system to monitor a resident of a dwelling comprising:
a sensor located at the dwelling to sense for resident activity at a location at the dwelling and coupled to save at one or more non-transitory memories, sensor information providing an indication of resident activity and time of resident activity at the location at the dwelling;
one or more computing machines;
non-transitory memory including instructions incorporated into the non-transitory memory, the instructions configuring the computing machine to perform operations comprising:
using a machine learning trained model, trained based at least in part upon resident activity at the location at the dwelling sensed by the sensor to learn an anticipated time of resident activity at the location of the dwelling, to identify the anticipated time of occurrence of resident activity at the location at the dwelling;
determining whether the sensor information indicates an occurrence of the anticipated resident activity within a predetermined time interval after the anticipated time of occurrence of the resident activity at the location at the dwelling; and
causing sending of an alert indicating a failed anticipated activity event, on a condition that the sensor data indicates no occurrence of the anticipated resident activity within the predetermined time interval after the anticipated time.

6. The system of claim 5, the operations further including:
receiving information indicating successful resolution of the failed anticipated activity event;
determining based in part upon the communication indicating successful resolution of the failed anticipated activity event whether the resident's anticipated activity pattern has changed;
based on a determination that the resident's anticipated activity pattern has changed, retraining the machine learning trained model.

7. A system to monitor a resident of a dwelling comprising:
a plurality of sensors located at the dwelling to sense for resident activity at different locations at the dwelling and coupled to save at one or more non-transitory memories sensor information providing an indication of occurrences and times of resident activity at the different locations at the dwelling;
one or more computing machines;
non-transitory memory including instructions incorporated into the non-transitory memory, the instructions configuring the computing machine to perform operations comprising:
using a machine learning trained model, trained based at least in part upon resident traversal activity between sensors at different locations of the dwelling to learn an anticipated traversal path ATP located at the dwelling the ATP having a first terminal point and a second terminal point and to learn a path traversal frequency (PTF) for the learned ATP, to identify the PTF for the ATP;
determining whether the sensor information indicates resident traversal of the ATP with a frequency that is within a predetermined range of the PTF; and
causing sending of an alert indicating a failed PTF event, on a condition that the sensor data indicates resident traversal of the ATP is not within the predetermined range of the PTF.

8. The system of claim 7,
wherein the plurality of sensors includes a plurality of motion sensors.

9. The system of claim 7 the operations further including:
receiving information indicating successful resolution of the failed PTF event;
determining based in part upon the communication indicating successful resolution of the failed PTF event whether the resident's PTF pattern has changed;
based on a determination that the resident's PTF pattern has changed, retraining the machine learning trained model.

10. A system to monitor a resident of a dwelling comprising:
a plurality of sensors located at the dwelling to sense for resident activity at different locations at the dwelling and coupled to save at one or more non-transitory memories, sensor information providing indications of occurrences and times of resident activity;
one or more computing machines;
non-transitory memory including instructions incorporated into the non-transitory memory, the instructions configuring the computing machine to perform operations comprising:
identifying locations at the dwelling of occurrences of resident movement activity and times of occurrences of the resident movement activity, based at least in part upon the sensor information produced using sensors located at the dwelling to sense resident movement activity at the identified locations;
using a machine learning trained model, trained based at least in part upon resident traversal activity between sensors at different locations of the dwelling to learn a plurality of anticipated traversal paths (ATPs) located at the dwelling each ATP having a first terminal point and a second terminal point, to identify for each occurrence of resident movement activity one or more ATPs based at least in part upon the identified location of the occurrence of the resident movement activity, the one or more identified ATPs each having a first terminal point associated with the identified location of the occurrence of the resident movement activity and having a second terminal point associated with a different location at the dwelling;

determining for each occurrence of resident movement activity whether the sensor information indicates an occurrence within a predetermined time interval after the occurrence of resident movement activity at a location at the dwelling corresponding to a second terminal point of at least one of the one or more ATPs identified for the occurrence of resident movement activity;

for each occurrence of resident movement activity, causing sending of an alert indicating a failed ATP traversal event, on a condition that the sensor data indicates for each of the one or more identified ATPs identified for the occurrence of resident movement activity, no occurrence within the predetermined time interval after the occurrence of resident movement activity, of resident movement activity at a location of the dwelling corresponding to the second terminal point of the identified ATP;

receiving information indicating successful resolution of one or more of the failed ATP events;

determining based in part upon the communication indicating successful resolution of one or more of the failed ATP events whether the resident's ATP pattern has changed; and based on a determination that the resident's ATP pattern has changed, retraining the machine learning trained model.

11. A system to monitor a resident of a dwelling comprising:

a sensor located at the dwelling to sense for resident activity at a location at the dwelling and coupled to save at one or more non-transitory memories, sensor information providing indications of occurrences and times of resident activity at the location at the dwelling;

one or more computing machines;

non-transitory memory including instructions incorporated into the non-transitory memory, the instructions configuring the computing machine to perform operations comprising:

using a machine learning trained model, trained based at least in part upon resident activity at the location at the dwelling sensed by the sensor to learn an anticipated time of resident activity at the location of the dwelling, to identify the anticipated time of occurrence of a recurrent resident activity at the location at the dwelling;

determining for each anticipated occurrence of the recurrent resident activity whether the sensor information indicates an occurrence of the anticipated recurrent resident activity;

for each occurrence of resident movement activity, causing sending of an alert indicating a failed anticipated recurrent activity event, on a condition that the sensor data indicates no occurrence of the anticipated recurrent resident activity;

receiving information indicating successful resolution of one or more of the failed anticipated recurrent activity events;

determining based in part upon the communication indicating successful resolution of one or more of the failed anticipated recurrent activity events whether the resident's anticipated resident activity pattern has changed; and based on a determination that the resident's anticipated resident activity pattern has changed, retraining the machine learning trained model.

12. A method to monitor a resident of a dwelling comprising:

using a plurality of sensors located at the dwelling to sense for resident activity at different locations at the dwelling and to produce for each sensor, sensor information providing indications of occurrences and times of resident activity;

identifying a location at the dwelling, of resident activity at a first time, based at least in part upon sensor information produced using a sensor located at the dwelling to sense resident activity at the identified location;

using a machine learning trained model, trained based at least in part upon resident traversal activity between sensors at different locations of the dwelling to learn a plurality of anticipated traversal paths (ATPs) located at the dwelling each ATP having a first terminal point and a second terminal point, to identify one or more ATPs based at least in part upon the identified location, the one or more identified ATPs each having a first terminal points associated with the identified location and having a second terminal point associated with a different location at the dwelling;

determining whether the sensor information indicates an occurrence within a predetermined time interval after the first time, of resident activity at a location at the dwelling corresponding to a second terminal point of at least one of the one or more identified ATPs; and causing sending of an alert indicating a failed ATP traversal event, on a condition that the sensor data indicates for each of the one or more identified ATPs, no occurrence within the predetermined time interval after the first time, of resident activity at a location of the dwelling corresponding to the second terminal point of the identified ATP.

13. The method of claim 12 the further including:

receiving information indicating successful resolution of the failed ATP traversal event;

determining based in part upon the communication indicating successful resolution of the failed ATP traversal event whether the resident's traversal activity pattern has changed;

based on a determination that the resident's traversal activity pattern has changed, retraining the machine learning trained model.

14. A method to monitor a resident of a dwelling comprising:

using a sensor located at the dwelling to sense for resident activity at a location at the dwelling and to produce sensor information providing an indication of resident activity and time of resident activity at the location at the dwelling;

using a machine learning trained model, trained based at least in part upon resident activity at the location at the dwelling sensed by the sensor to learn an anticipated time of resident activity at the location of the dwelling, to identify the anticipated time of occurrence of resident activity at the location at the dwelling;

determining whether the sensor information indicates an occurrence of the anticipated resident activity within a predetermined time interval after the anticipated time of occurrence of the resident activity at the location at the dwelling; and causing sending of an alert indicating a failed anticipated activity event, on a condition that the sensor data indicates no occurrence of the anticipated resident activity within the predetermined time interval after the anticipated time.

15. The method of claim 12, the operations further including:
receiving information indicating successful resolution of the failed anticipated activity event;
determining based in part upon the communication indicating successful resolution of the failed anticipated activity event whether the resident's anticipated activity pattern has changed;
based on a determination that the resident's anticipated activity pattern has changed, retraining the machine learning trained model.

16. A method to monitor a resident of a dwelling comprising:
using a plurality of sensors located at the dwelling to sense for resident activity at different locations at the dwelling and to produce for each sensor, sensor information providing an indication of occurrences and times of resident activity at the different locations at the dwelling;
using a machine learning trained model, trained based at least in part upon resident traversal activity between sensors at different locations of the dwelling to learn an anticipated traversal path ATP located at the dwelling the ATP having a first terminal point and a second terminal point and to learn a path traversal frequency (PTF) for the learned ATP, to identify the PTF for the ATP;
determining whether the sensor information indicates resident traversal of the ATP with a frequency that is within a predetermined range of the PTF; and
causing sending of an alert indicating a failed PTF event, on a condition that the sensor data indicates resident traversal of the ATP is not within the predetermined range of the PTF.

17. The method of claim 16 the operations further including:
receiving information indicating successful resolution of the failed PTF event;
determining based in part upon the communication indicating successful resolution of the failed PTF event whether the resident's PTF pattern has changed;
based on a determination that the resident's PTF pattern has changed, retraining the machine learning trained model.

18. A method to monitor a resident of a dwelling comprising:
using a plurality of sensors located at the dwelling to sense for resident activity at different locations at the dwelling and to produce for each sensor, sensor information providing indications of occurrences and times of resident activity;
identifying locations at the dwelling of occurrences of resident movement activity and times of occurrences of the resident movement activity, based at least in part upon sensor information produced using sensors located at the dwelling to sense resident movement activity at the identified locations;
using a machine learning trained model, trained based at least in part upon resident traversal activity between sensors at different locations of the dwelling to learn a plurality of anticipated traversal paths (ATPs) located at the dwelling each ATP having a first terminal point and a second terminal point, to identify for each occurrence of resident movement activity one or more ATPs based at least in part upon the identified location of the occurrence of the resident movement activity, the one or more identified ATPs each having a first terminal point associated with the identified location of the occurrence of the resident movement activity and having a second terminal point associated with a different location at the dwelling;
determining for each occurrence of resident movement activity whether the sensor information indicates an occurrence within a predetermined time interval after the occurrence of resident movement activity at a location at the dwelling corresponding to a second terminal point of at least one of the one or more ATPS identified for the occurrence of resident movement activity;
for each occurrence of resident movement activity, causing sending of an alert indicating a failed ATP traversal event, on a condition that the sensor data indicates for each of the one or more identified ATPs identified for the occurrence of resident movement activity, no occurrence within the predetermined time interval after the occurrence of resident movement activity, of resident movement activity at a location of the dwelling corresponding to the second terminal point of the identified ATP;
receiving information indicating successful resolution of one or more of the failed ATP events;
determining based in part upon the communication indicating successful resolution of one or more of the failed ATP events whether the resident's ATP pattern has changed; and
based on a determination that the resident's ATP pattern has changed, retraining the machine learning trained model.

19. A method to monitor a resident of a dwelling comprising:
using a sensor located at the dwelling to sense for resident activity at a location at the dwelling and to produce sensor information providing an indication of resident activity and time of resident activity at the location at the dwelling;
using a machine learning trained model, trained based at least in part upon resident activity at the location at the dwelling sensed by the sensor to learn an anticipated time of resident activity at the location of the dwelling, to identify the anticipated time of occurrence of a recurrent resident activity at the location at the dwelling;
determining for each anticipated occurrence of the recurrent resident activity whether the sensor information indicates an occurrence of the anticipated recurrent resident activity;
for each occurrence of resident movement activity, causing sending of an alert indicating a failed anticipated recurrent activity event, on a condition that the sensor data indicates no occurrence of the anticipated recurrent resident activity;
receiving information indicating successful resolution of one or more of the failed anticipated recurrent activity events;
determining based in part upon the communication indicating successful resolution of one or more of the failed anticipated recurrent activity events whether the resident's anticipated resident activity pattern has changed; and based on a determination that the resident's anticipated resident activity pattern has changed, retraining the machine learning trained model.

\* \* \* \* \*